US007407935B2

(12) United States Patent
Olson et al.

(10) Patent No.: US 7,407,935 B2
(45) Date of Patent: Aug. 5, 2008

(54) RICIN TOXIN A-CHAIN FRAGMENT FOR USE AS A VACCINE

(75) Inventors: Mark A. Olson, Middletown, MD (US); Charles B. Millard, Frederick, MD (US); Michael P. Byrne, New Market, MD (US); Robert W. Wannemacher, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 486 days.

(21) Appl. No.: 10/923,022

(22) Filed: Aug. 23, 2004

(65) Prior Publication Data

US 2006/0009619 A1 Jan. 12, 2006

Related U.S. Application Data

(63) Continuation of application No. 10/083,336, filed on Feb. 27, 2002, now Pat. No. 6,869,787.

(51) Int. Cl.
*A61K 38/16* (2006.01)
*A61K 36/47* (2006.01)
*C12P 21/02* (2006.01)
(52) U.S. Cl. .................. 514/12; 350/370; 435/69.1
(58) Field of Classification Search .................. 435/4, 435/6, 183, 190, 200, 252–3, 320.1, 69.1; 530/350, 370; 424/184.1, 190.1; 514/12
See application file for complete search history.

(56) References Cited

U.S. PATENT DOCUMENTS 4,080,457 A 3/1978 Harrison et al.
4,689,401 A 8/1987 Ferris
4,962,188 A 10/1990 Frankel
5,376,546 A * 12/1994 Bernhard et al. ............ 435/199
5,416,202 A * 5/1995 Bernhard et al. ........... 536/23.2
5,453,271 A 9/1995 Lemley et al.
5,547,867 A 8/1996 Kara et al.

(Continued)

FOREIGN PATENT DOCUMENTS

WO  WO 88/09344  12/1988

(Continued)

OTHER PUBLICATIONS

Roberts et al. (GenBank Acc No. P06750, Jan. 1, 1988).*

(Continued)

*Primary Examiner*—Rebecca E. Prouty
*Assistant Examiner*—Rosanne Kosson
(74) *Attorney, Agent, or Firm*—Elizabeth Arwine

(57) ABSTRACT

Disclosed herein are polypeptides and variants thereof comprising a polypeptide sequence having substantial identity to ricin A chain (RTA) that lack detectable N-glycosidase-rRNA activity or exhibit reduced N-glycosidase-rRNA activity as compared to controls and methods of making and using thereof. The polypeptides and variants have a greater solubility in aqueous solutions of physiological pH and ionic strength than RTA and also retain the integrity of the neutralizing immunological epitope of wild type RTA. Also disclosed are immunogenic compositions that may be used to immunize a subject against ricin intoxication. Methods of immunizing against, treating, and preventing ricin intoxication are disclosed.

5 Claims, 2 Drawing Sheets

U.S. PATENT DOCUMENTS

| | | | |
|---|---|---|---|
| 5,621,083 A * | 4/1997 | Better et al. | 530/391.9 |
| 5,622,838 A | 4/1997 | Lord et al. | |
| 5,626,844 A | 5/1997 | Lemley et al. | |
| 5,646,026 A | 7/1997 | Walsh et al. | |
| 5,744,580 A * | 4/1998 | Better et al. | 530/377 |
| 5,756,699 A * | 5/1998 | Better et al. | 536/23.4 |
| 5,837,491 A * | 11/1998 | Better et al. | 435/69.1 |
| 5,877,305 A * | 3/1999 | Huston et al. | 536/23.53 |
| 6,060,066 A | 5/2000 | Lemley, Jr. et al. | |
| 6,084,073 A | 7/2000 | Piatak, Jr. | |
| 6,333,303 B1 | 12/2001 | Borgford | |
| 6,531,125 B1 | 3/2003 | Borgford | |

FOREIGN PATENT DOCUMENTS

| | | |
|---|---|---|
| WO | WO 00/53215 | 9/2000 |

OTHER PUBLICATIONS

Wood et al. (GenBank Acc No. P28590, Dec. 1, 1992).*

Aboud-Pirak, E, et al. (1993) "Identification of Neutralizing Epitope on a Chain and Application", Medical Defense Bioscience Review, Proceedings (5):1431-1440.

Afrin, LB, et al (1994) "Expression of Oligohistidine-Tagged Ricin B. Chain in *Spodoptera frugiperda*" Bioconjugate Chem. 5(6):539-546.

Appukuttan, PS, et al (1979) "Separation of Polypeptide Chains of Ricin and the Interaction of the A Chain With Cibacron Blue $F_3GA$" Biochimica et Biophysica Acta, 580:10-14.

Argent, RH, et al. (1995) "Purification of Recombinant Ricin A Chain after Reassociation with Ricin B Chain" Analytical Biochemistry (224):459-460.

Blakey, DC, et al. (1987) "Effect of Chemical Deglycosylation of Ricin A Chain on the in Vivo Fate and Cytotoxic Activity of an Immunotoxin Composed of Ricin A Chain and Anti-Thy 1.1 Antibody", Cancer Research (47):947-952.

Baluna, R, et al. (1999) "Evidence for a structural motif in toxins and interleukin-2 that may be responsible for binding to endothelial cells and initiating vascular leak syndrome", Proc. Natl. Acad. Sci. (96):3957-3963.

Bradley, JL, et al. (1989) "Site-directed mutagenesis at amino terminus of recombinant ricin A chain" Int. J. Peptide Protein Res. (34):2-5.

Brigotti, M, et al. (1998) "A rapid and sensitive method to measure the enzymatic activity of ribosome-inactivating proteins" Nucleic Acids Research, (26):18.

"Chemical Warfare Agents, and Related Chemical Problems, Parts I-II", Ricin, Chapter 12, Summary Technical Report of Div. 9, NDRA, vol. 1 (1946).

Byers, V, et al. (1993) "Suppression of Antibody Responses to Ricin A Chain (RTA) by Monoclonal Anti-RTA Antibodies" Journal of Clinical Immunology, (13):6.

Chang, MS, et al. (1987) "Cloning and expression of recombinant, functional ricin B chain" Proc. Natl. Acad. Sci, (84):5640-5644.

Chanh, TC, et al. (1993) "Monoclonal Antibody Prophylaxis Against the In Vivo Toxicity of Ricin in Mice" Immunological Investigations 22(1):63-72.

Colombatti, M, et al. (1986) "Monoclonal Antibodies Against Ricin: Effects on Toxin Function" Hybridoma 5(1): 9-19.

Day, PJ, et al. (1996) "Structure and Activity of an Active Site Substitution of Ricin A Chain" Biochemistry (35): 11098-11103.

Despeyroux, D, et al. (2000) "Characterization of Ricin Heterogeneity by Electrospray Mass Spectrometry, Capillary Electrophoresis, and Resonant Mirror", Analytical Biochemistry (279):23-36.

Emmanuel, F, et al. (1988) "Separation of Ricin A- and B-Chains after Dithiothreitol Reduction" Analytical Biochemistry (173):134-141.

Ferrini, JB, et al. (1995) "Expression of functional ricin B chain using the baculovirus system" Eur. J. Biochem. (233):772-777.

Foxwell, BM, et al. (1987) "The preparation of deglycosylated ricin by recombination of glycosidase-treated A- and B-chains: effects of deglycosylation on toxicity and in vivo distribution" Biochimica et Biophysica Acta (923):59-65.

Foxwell, BMJ, et al. (1985) "The removal of carbohydrates from ricin with endoglycosidases H, F and D and α-mannosidase", Biochimica et Biophysica Acta (840):193-203.

Foxwell, BMJ, et al. (1985) "The Use of Anti-ricin Antibodies to Protect Mice Intoxicated with Ricin" Toxicology, (34):79-88.

Frankel, A, et al. (1994) "Expression of ricin B chain in *Spodoptera frugiperda*" Biochem. J. (303):787-794.

Frankel, A, et al. (1989) "Selection and Characterization of Ricin Toxin A-Chain Mutations in *Saccharomyces cerevisiae*" Molecular and Cellular Biology, 9(2):415-420.

Franz, DR, et al. "Ricin Toxin"Medical Aspects of Chemical & Biologcal Warfare 631-642.

Frénoy, JP (1986) "Effect of physical environment on the conformation of ricin" Biochem. J. (240):221-226.

Frénoy, JP et al. (1986) "Structure and stability of *Ricinus communis* haemagglutinin" Biochem. J. (240)227-231.

Frigerio, L, et al. (2001) "The Internal Propeptide of the Ricin Precursor Carries a Sequence-Specific Determinant for Vacuolar Sorting" *Plant Physiology* (126):167-175.

Fulton, R.J., et al. (1986) "Purification of Ricin $A_1$, $A_2$, and B Chains and Characterization of Their Toxicity" The Journal of Biological Chemistry 261 (12):5314-5319.

Furukawa-Stoffer, TL, et al. (1999) "A Novel Biological-Based Assay for the Screening of Neutralizing Antibodies to Ricin" Hybridoma 18(6):505-510.

Griffiths, GD, et al. (1999) "Comparison of the quality of protection elicited by toxoid and peptide liposomal vaccine formulations against ricin as assessed by markers of inflammation" Vaccine (17):2562-2568.

Griffiths, GD, et al. (1995) "Protection against inhalation toxicity of ricin and abrin by immunisation" Human & Experimental Toxicology (14):155-164.

Griffiths, GD, et al. (1997) "Liposomally-encapsulated ricin toxoid vaccine delivered intratracheally elicits a good immune response and protects against a lethal plumonary dose of ricin toxin" Vaccine 15(17/18):1933-1939.

Griffiths, GD, et al. "The inhalation toxicology of the castor bean toxin, ricin, and protection by vaccination" Journal of Defense Science 1(2):227-235.

Hale, ML (2001) "Microtiter-Based Assay for Evaluating the Biological Activity of Ribosome-Inactivating Proteins" Pharmacology & Toxicology (88):255-260.

Hewetson, JF, et al. (1993) "Protection of mice from inhaled ricin by vaccination with ricin or by passive treatment with heterologous antibody" Vaccine 11(7):743-746.

Hussain, K, et al. (1989) "Expression of ricin B chain in *Escherichia coli*" FEBS Letters 244(2):383-387.

Katzin, BJ, et al. (1991) "Structure of Ricin A-Chain at 2.5 Å"Proteins: Structure, Function, and Genetics (10):251-259.

Kim, Y, et al. (1992) "Analysis of several key active site residues of ricin A chain by mutagenesis and X-ray crystallography" Protein Engineering 5(8):775-779.

Kim, Y, et al. (1992) "Structure of a Ricin Mutant Showing Rescue of Activity by a Noncatalytic Residue" Biochemistry (31):3294-3296.

Kurinov, IV, et al. (1999) X-ray crystallographic analysis of the structural basis for the interaction of pokeweed antiviral protein with guanine residues of ribsomal RNA Protein Science (8):2399-2405.

Lamb, FI, et al. (1985) "Nucleotide sequence of cloned cDNA coding for preproricin" Bar J. Biochem 1(48):265-270.

Langer, M, et al. (1996) "A Nonradioactive Assay for Ribosome-Inactivating Proteins" Analytical Biochemistry (243):150-153.

Langer, M. et al. "A Nonradioactive Assay for Ribosome-Inactivating Proteins" Brain GmbH, Bio. Res. & Info. Network.

Lebeda, FJ, et al. (1999) "Prediction of a conserved, neutralizing epitope in ribosome-inactivating proteins" Int'l. Journal of Bio. Macromolecules (24):19-26.

Lemley, PV, et al. (1992) "Mice are actively immunized after passive monoclonal antibody prophylaxis and ricin toxin challenge" Immunology (76):511-513.

Lemley, PV, et al. (1992) "Prophylactic and therapeutic efficacy of an avian antitoxin in ricin intoxication" Therapeutic Immunology (2):59-66.

Lemley, PV, et al. (1994) "Identification and Characterization of A Monoclonal Antibody that Neutralizes Ricin Toxicity in Vitro and in Vivo" Hybridoma 13(5):417-421.

Lewis, MS, et al. (1986) "Thermodynamics and the Role of the Disulfide Bond Toxicity" Ricin Subunit Association 11571-11577.

Mlsna, D, et al. (1993) "Structure of recombinant ricin a chain at 2.3 Å" Protein Science (2):429-435.

Montfort, W, et al. (1987) The Three-dimensional Structure of Ricin at 2.8 Å The Journal of Biological Chemistry 262(11):5398-5403.

O'Hare, M, et al. (1992) "Biological activity of recombinant *Ricinus communis* agglutinin A chain produced in *Escherichia coli*" FEBS Letters 299(3):209-212.

Olson, MA (2001) "Electrostatic effects on the free-energy balance in folding a ribosome-inactivating protein" Biophysical Chemistry (91):219-229.

Olson, MA (2001) "Calculations of Free-Energy Contributions to Protein-RNA Complex Stabilization" Biophysical Journal (81):1841-1853.

Olson, MA (1999) "Free Energy Determinants of Binding the rRNA Substrate and Small Ligands to Ricin A-Chain" Biophysical Journal (76):28-39.

Olson, MA (1997) "Ricin A-Chain Structural Determinant for Binding Substrate Analogues: A Molecular Dynamics Simulation Anaylsis" Proteins: Structure, Function, and Genetics (27):80-95.

Olsnes, S, et al. (2001) "Ricin" Toxicon (39):1723-1728.

Pastan, I, et al. (1992) "Recombinant Toxins as Novel Therapeutic Agents" Annu. Rev. Biochem (61):331-54.

Pistak, M, et al. (1988) "Expression of Soluble and Fully Functional Ricin A Chain in *Escherichia coli* is Temperature-sensitive" The Journal of Biological Chemistry 263(10):4837-4843.

Poli, MA, et al. (1996) "Aerosolized Specific Antibody Protects Mice From Lung Injury Associated With Aerosolized Ricin Exposure" Toxicon 34(9):1037-1044.

Ready, MP, et al. (1991) "Site-Directed Mutagenesis of Ricin A-Chain and Implications for the Mechanism of Action" Proteins: Structure, Function, and Genetics (10):270-278.

Richardson, PT, et al. (1988) "The expression of functional ricin B-chain in *Saccharomyces cerevisiae*" Biochimica et Biophysica Acta (950):385-394.

Robertus, J, et al. (1987) "Crystallization of Ricin A Chain Obtained from a Cloned Gene Expressed in *Escherichia coli*" The Journal of Biological Chemistry 262(1):19-20.

Rutenber, E, et al. (1991) "Crystallographic Refinement of Ricin to 2.5 Å" Proteins: Structure, Function, and Genetics (10):240-250.

Rutenber, E, et al. (1991) "Structure of Ricin B-Chain at 2.5 Å Resolution" Proteins: Structure, Function, and Genetics (10):260-269.

Schlossman, D et al. (1989) "Role of Glutamic Acid 177 of the Recin Toxin A Chain in Enzymatic Inactivation of Ribosomes" Molecular and Cellular Biology 9(11):5012-5021.

Schramm, V (1997) "Enzymatic N-riboside scission in RNA and RNA precursors" Curr. Opin. Chem. Biol. 1:323-331.

Simmons, BM, et al. (1985) A Single Affinity Column Step Method for the Purification of Ricin Toxin from Castor Beans (*Ricinus communis*) Analytical Biochemistry (146):206-210.

Smallshaw, JE, et al. (2002) "A novel recombinant vaccine which protects mice against ricin intoxication" Vaccine (20):3422-3427.

Tagge, E, et al. (1997) "Synthesis of Green Fluorescent Protein-Ricin and Monitoring of Its Intracellular Trafficking" Bioconjugate Chem. (8):743-750.

Tagge, et al. (1996) "Preproricin Expressed in *Nicotiana tabacum* Cells in Vitro Fully Processed and Biologically Active" In Vitro Plant Cell Expression of Preproricin (8):109-118.

Vitetta, ES, et al. (1990) "Expression and functional properties of genetically engineered ricin B chain lacking galactose-binding activity" Biochimica et Biophysica Acta, (1049):151-157.

Vitetta, E, et al. Vaccines to Protect Against Aerosolized Ricin UTSD:0723.

Vogel, P, et al. (1996) "Comparison of the Pulmonary Distribution and Efficacy of Antibodies Given to Mice by Intratracheal Instillation or Aerosol Inhalation" Lab. Animal Science 46(5):516-523.

Wales, R, et al. (1994) "Ricin B. chain fragments expressed in *Escherichia coli* are able to bind free galactose in contrast to the full length polypeptide" Glycoconjugate Journal (11):274-281.

Weston, SA, et al. (1994) "X-ray Structure of Recombinant Ricin A-Chain at 1.8 Å Resolution" J. Mol. Bio. (244):410-422.

Wihelmsen, CL (2000) "Respiratory Pathogenesis"

Wilhelmsen, CL, et al. (1996) "Lesions of Acute Inhaled Lethal Ricin Intoxication in Rhesus Monkeys" Vet Pathol (33):296-302.

Yan, X, et al. (1997) "Structure-based Identification of a Ricin Inhibitor" J. Mol. Biol. (266):1043-1049.

Zamboni, M et al., (1989) "High pressure-liquid-chromatographic and fluorimetric methods for the determination of adenine released from ribosomes by ricin and gelonin" Chem. J. (259):639-643.

Chen, X., et al. (1998) "Ricin A-Chain: Kinetics, Mechanism, and RNA Stem—Loop Inhibitors" Biochemistry 37:11605-11613.

Gould, J., et al. (1991) "Alteration of an amino acid residue outside the active site of the ricin A chain reduces its toxicity towards yeast ribosomes" Mol. Gen. Genet. 230:81-90.

Lord, J., et al. (1991) "Ribosome inactivating proteins of plants" Cell Biology 2:15-22.

Robertus, Jon. (1991) "The structure and action of ricin, a cytotoxic N-glycosidase" Cell Biology 2:23-30.

Ready, et al., "Site-Directed Mutagenesis of Ricin A-Chain and Implications for the Mechanism of Action", Proteins, 1991, vol. 10, pp. 270-278.

Kim et al., "Structure of a Ricin Mutant Showing Rescue of Activity by a Noncatalytic Residue", Biochemistry, 1992, vol. 31, pp. 3294-3296.

Schlossman et al., "Role of Glutamic Acid 177 of the Ricin Toxin A Chain in Enzymatic Inactivation of Ribosomes", Mol. Cell. Biol. Nov. 1989, vol. 9, No. 11, pp. 5012-5021.

Kim et al., "Analysis of Several Key Active Site Residues of Ricin A Chain By Mutagenesis and X-ray Crystallography", Protein Eng. 1992, vol. 5, No. 8, pp. 775-779.

Morris et al., Determination by Systematic Deletion of the Amino Acids Essential for Catalysis by Ricin A Chain, Proc. Natl. Acad. Sci Jun. 1992, vol. 89, pp. 4869-4873.

Hewetson, J.F. et al. (1993) "Protection of Mice from Inhaled Ricin by Vaccination with Ricin or By Passive Treatment with Heterologous Antibody" Vaccine 11(7):743-746.

Lemley, P.V. et al. (1994) "Identification and Characterization of a Monoclonal Antibody that Neutralizes Ricin Toxicity In Vitro and In Vivo" Hybridoma 13(5):417-421.

Morris et al. (1992) "Determination by systematic deletion of the amino acids essential for catalysis by ricin A chain" PNAS USA 89:4869-4873.

* cited by examiner

SEQUENCE LISTING

<160> NUMBER OF SEQ ID NOS: 15

<210> SEQ ID NO 1
<211> LENGTH: 576
<212> TYPE: PRT
<213> ORGANISM: Ricinus communis

<400> SEQUENCE: 1

```
Met Lys Pro Gly Gly Asn Thr Ile Val Ile Trp Met Tyr Ala Val Ala
  1               5                  10                  15

Thr Trp Leu Cys Phe Gly Ser Thr Ser Gly Trp Ser Phe Thr Leu Glu
             20                  25                  30

Asp Asn Asn Ile Phe Pro Lys Gln Tyr Pro Ile Ile Asn Phe Thr Thr
         35                  40                  45

Ala Gly Ala Thr Val G

```
Leu Ile Arg Pro Val Val Pro Asn Phe Asn Ala Asp Val Cys Met Asp
305                 310                 315                 320

Pro Glu Pro Ile Val Arg Ile Val Gly Arg Asn Gly Leu Cys Val Asp
            325                 330                 335

Val Arg Asp Gly Arg Phe His Asn Gly Asn Ala Ile Gln Leu Trp Pro
        340                 345                 350

Cys Lys Ser Asn Thr Asp Ala Asn Gln Leu Trp Thr Leu Lys Arg Asp
    355                 360                 365

Asn Thr Ile Arg Ser Asn Gly Lys Cys Leu Thr Thr Tyr Gly Tyr Ser
370                 375                 380

Pro Gly Val Tyr Val Met Ile Tyr Asp Cys Asn Thr Ala Ala Thr Asp
385                 390                 395                 400

Ala Thr Arg Trp Gln Ile Trp Asp Asn Gly Thr Ile Ile Asn Pro Arg
            405                 410                 415

Ser Ser Leu Val Leu Ala Ala Thr Ser Gly Asn Ser Gly Thr Thr Leu
        420                 425                 430

Thr Val Gln Thr Asn Ile Tyr Ala Val Ser Gln Gly Trp Leu Pro Thr
    435                 440                 445

Asn Asn Thr Gln Pro Phe Val Thr Thr Ile Val Gly Leu Tyr Gly Leu
450                 455                 460

Cys Leu Gln Ala Asn Ser Gly Gln Val Trp Ile Glu Asp Cys Ser Ser
465                 470                 475                 480

Glu Lys Ala Glu Gln Gln Trp Ala Leu Tyr Ala Asp Gly Ser Ile Arg
            485                 490                 495

Pro Gln Gln Asn Arg Asp Asn Cys Leu Thr Ser Asp Ser Asn Ile Arg
        500                 505                 510

Glu Thr Val Val Lys Ile Leu Ser Cys Gly Pro Ala Ser Ser Gly Gln
    515                 520                 525

Arg Trp Met Phe Lys Asn Asp Gly Thr Ile Leu Asn Leu Tyr Ser Gly
530                 535                 540

Leu Val Leu Asp Val Arg Ala Ser Asp Pro Ser Leu Lys Gln Ile Ile
545                 550                 555                 560

Leu Tyr Pro Leu His Gly Asp Pro Asn Gln Ile Trp Leu Pro Leu Phe
            565                 570                 575

<210> SEQ ID NO 2
<211> LENGTH: 179
<212> TYPE: PRT
<213> ORGANISM: Ricinus communis

<400> SEQUENCE: 2

Met Lys Pro Gly Gly Asn Thr Ile Val Ile Trp Met Tyr Ala Val Ala
1               5                   10                  15

Thr Trp Leu Cys Phe Gly Ser Thr Ser Gly Trp Ser Phe Thr Leu Glu
            20                  25                  30

Asp Asn Asn Ile Phe Pro Lys Gln Tyr Pro Ile Ile Asn Phe Thr Thr
        35                  40                  45

Ala Gly Ala Thr Val Gln Ser Tyr Thr Asn Phe Ile Arg Ala Val Arg
    50                  55                  60

Gly Arg Leu Thr Thr Gly Ala Asp Val Arg His Glu Ile Pro Val Leu
65                  70                  75                  80

Pro Asn Arg Val Gly Leu Pro Ile Asn Gln Arg Phe Ile Leu Val Glu
            85                  90                  95

Leu Ser Asn His Ala Glu Leu Ser Val Thr Leu Ala Leu Asp Val Thr
```

```
            100                 105                 110
Asn Ala Tyr Val Val Gly Tyr Arg Ala Gly Asn Ser Ala Tyr Phe Phe
            115                 120                 125

His Pro Asp Asn Gln Glu Asp Ala Glu Ala Ile Thr His Leu Phe Thr
130                 135                 140

Asp Val Gln Asn Arg Tyr Thr Phe Ala Phe Gly Gly Asn Tyr Asp Arg
145                 150                 155                 160

Leu Glu Gln Leu Ala Gly Asn Leu Arg Glu Asn Ile Glu Leu Gly Asn
                165                 170                 175

Gly Pro Leu

<210> SEQ ID NO 3
<211> LENGTH: 198
<212> TYPE: PRT
<213> ORGANISM: Ricinus communis

<400> SEQUENCE: 3

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Arg
        35                  40                  45

Val Gly Leu Pro Ile Asn Gln Arg Phe Ile Leu Val Glu Leu Ser Asn
    50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser
        195

<210> SEQ ID NO 4
<211> LENGTH: 188
<212> TYPE: PRT
<213> ORGANISM: Ricinus communis

<400> SEQUENCE: 4

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Val Leu Pro Asn Arg Val Gly Leu Pro Ile Asn Gln Arg Phe Ile
        35                  40                  45
```

```
Leu Val Glu Leu Ser Asn His Ala Glu Leu Ser Val Thr Leu Ala Leu
 50                  55                  60

Asp Val Thr Asn Ala Tyr Val Gly Tyr Arg Ala Gly Asn Ser Ala
 65                  70                  75                  80

Tyr Phe Phe His Pro Asp Asn Gln Glu Asp Ala Glu Ala Ile Thr His
                 85                  90                  95

Leu Phe Thr Asp Val Gln Asn Arg Tyr Thr Phe Ala Phe Gly Gly Asn
            100                 105                 110

Tyr Asp Arg Leu Glu Gln Leu Ala Gly Asn Leu Arg Glu Asn Ile Glu
        115                 120                 125

Leu Gly Asn Gly Pro Leu Glu Glu Ala Ile Ser Ala Leu Tyr Tyr
    130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185

<210> SEQ ID NO 5
<211> LENGTH: 199
<212> TYPE: PRT
<213> ORGANISM: Ricinus communis

<400> SEQUENCE: 5

Met Ile Phe Pro Lys Gln Tyr Pro Ile Ile Asn Phe Thr Thr Ala Gly
  1               5                  10                  15

Ala Thr Val Gln Ser Tyr Thr Asn Phe Ile Arg Ala Val Arg Gly Arg
             20                  25                  30

Leu Thr Thr Gly Ala Asp Val Arg His Glu Ile Pro Val Leu Pro Asn
         35                  40                  45

Arg Val Gly Leu Pro Ile Asn Gln Arg Phe Ile Leu Val Glu Leu Ser
 50                  55                  60

Asn His Ala Glu Leu Ser Val Thr Leu Ala Leu Asp Val Thr Asn Ala
 65                  70                  75                  80

Tyr Val Val Gly Tyr Arg Ala Gly Asn Ser Ala Tyr Phe Phe His Pro
                 85                  90                  95

Asp Asn Gln Glu Asp Ala Glu Ala Ile Thr His Leu Phe Thr Asp Val
            100                 105                 110

Gln Asn Arg Tyr Thr Phe Ala Phe Gly Gly Asn Tyr Asp Arg Leu Glu
        115                 120                 125

Gln Leu Ala Gly Asn Leu Arg Glu Asn Ile Glu Leu Gly Asn Gly Pro
    130                 135                 140

Leu Glu Glu Ala Ile Ser Ala Leu Tyr Tyr Ser Thr Gly Gly Thr
145                 150                 155                 160

Gln Leu Pro Thr Leu Ala Arg Ser Phe Ile Ile Cys Ile Gln Met Ile
                165                 170                 175

Ser Glu Ala Ala Arg Phe Gln Tyr Ile Glu Gly Glu Met Arg Thr Arg
            180                 185                 190

Ile Arg Tyr Asn Arg Arg Ser
        195

<210> SEQ ID NO 6
<211> LENGTH: 189
<212> TYPE: PRT
```

<213> ORGANISM: Ricinus communis

<400> SEQUENCE: 6

```
Met Ile Phe Pro Lys Gln Tyr Pro Ile Ile Asn Phe Thr Thr Ala Gly
 1               5                  10                  15

Ala Thr Val Gln Ser Tyr Thr Asn Phe Ile Arg Ala Val Arg Gly Arg
             20                  25                  30

Leu Thr Val Leu Pro Asn Arg Val Gly Leu Pro Ile Asn Gln Arg Phe
         35                  40                  45

Ile Leu Val Glu Leu Ser Asn His Ala Glu Leu Ser Val Thr Leu Ala
     50                  55                  60

Leu Asp Val Thr Asn Ala Tyr Val Val Gly Tyr Arg Ala Gly Asn Ser
 65                  70                  75                  80

Ala Tyr Phe Phe His Pro Asp Asn Gln Glu Asp Ala Glu Ala Ile Thr
                 85                  90                  95

His Leu Phe Thr Asp Val Gln Asn Arg Tyr Thr Phe Ala Phe Gly Gly
            100                 105                 110

Asn Tyr Asp Arg Leu Glu Gln Leu Ala Gly Asn Leu Arg Glu Asn Ile
        115                 120                 125

Glu Leu Gly Asn Gly Pro Leu Glu Glu Ala Ile Ser Ala Leu Tyr Tyr
    130                 135                 140

Tyr Ser Thr Gly Gly Thr Gln Leu Pro Thr Leu Ala Arg Ser Phe Ile
145                 150                 155                 160

Ile Cys Ile Gln Met Ile Ser Glu Ala Ala Arg Phe Gln Tyr Ile Glu
                165                 170                 175

Gly Glu Met Arg Thr Arg Ile Arg Tyr Asn Arg Arg Ser
            180                 185
```

<210> SEQ ID NO 7
<211> LENGTH: 198
<212> TYPE: PRT
<213> ORGANISM: Ricinus communis

<400> SEQUENCE: 7

```
Met Val Pro Lys Gln Tyr Pro Ile Ile Asn Phe Thr Thr Ala Gly Ala
 1               5                  10                  15

Thr Val Gln Ser Tyr Thr Asn Phe Ile Arg Ala Val Arg Gly Arg Leu
             20                  25                  30

Thr Thr Gly Ala Asp Val Arg His Glu Ile Pro Val Leu Pro Asn Arg
         35                  40                  45

Val Gly Leu Pro Ile Asn Gln Arg Phe Ile Leu Val Glu Leu Ser Asn
     50                  55                  60

His Ala Glu Leu Ser Val Thr Leu Ala Leu Asp Val Thr Asn Ala Tyr
 65                  70                  75                  80

Val Val Gly Tyr Arg Ala Gly Asn Ser Ala Tyr Phe Phe His Pro Asp
                 85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
```

```
                    165                 170                 175
Glu Ala Ala Arg Phe Gln Tyr Ile Glu Gly Glu Met Arg Thr Arg Ile
            180                 185                 190

Arg Tyr Asn Arg Arg Ser
        195

<210> SEQ ID NO 8
<211> LENGTH: 188
<212> TYPE: PRT
<213> ORGANISM: Ricinus communis

<400> SEQUENCE: 8

Met Val Pro Lys Gln Tyr Pro Ile Ile Asn Phe Thr Thr Ala Gly Ala
  1               5                  10                  15

Thr Val Gln Ser Tyr Thr Asn Phe Ile Arg Ala Val Arg Gly Arg Leu
            20                  25                  30

Thr Val Leu Pro Asn Arg Val Gly Leu Pro Ile Asn Gln Arg Phe Ile
        35                  40                  45

Leu Val Glu Leu Ser Asn His Ala Glu Leu Ser Val Thr Leu Ala Leu
    50                  55                  60

Asp Val Thr Asn Ala Tyr Val Val Gly Tyr Arg Ala Gly Asn Ser Ala
 65                  70                  75                  80

Tyr Phe Phe His Pro Asp Asn Gln Glu Asp Ala Glu Ala Ile Thr His
                85                  90                  95

Leu Phe Thr Asp Val Gln Asn Arg Tyr Thr Phe Ala Phe Gly Gly Asn
            100                 105                 110

Tyr Asp Arg Leu Glu Gln Leu Ala Gly Asn Leu Arg Glu Asn Ile Glu
        115                 120                 125

Leu Gly Asn Gly Pro Leu Glu Glu Ala Ile Ser Ala Leu Tyr Tyr Tyr
    130                 135                 140

Ser Thr Gly Gly Thr Gln Leu Pro Thr Leu Ala Arg Ser Phe Ile Ile
145                 150                 155                 160

Cys Ile Gln Met Ile Ser Glu Ala Ala Arg Phe Gln Tyr Ile Glu Gly
                165                 170                 175

Glu Met Arg Thr Arg Ile Arg Tyr Asn Arg Arg Ser
            180                 185

<210> SEQ ID NO 9
<211> LENGTH: 185
<212> TYPE: PRT
<213> ORGANISM: Ricinus communis

<400> SEQUENCE: 9

Ile Phe Pro Lys Gln Tyr Pro Ile Ile Asn Phe Thr Thr Ala Gly Ala
  1               5                  10                  15

Thr Val Gln Ser Tyr Thr Asn Phe Ile Arg Ala Val Arg Gly Arg Leu
            20                  25                  30

Thr Asn Arg Val Gly Leu Pro Ile Asn Gln Arg Phe Ile Leu Val Glu
        35                  40                  45

Leu Ser Asn His Ala Glu Leu Ser Val Thr Leu Ala Leu Asp Val Thr
    50                  55                  60

Asn Ala Tyr Val Val Gly Tyr Arg Ala Gly Asn Ser Ala Tyr Phe Phe
 65                  70                  75                  80

His Pro Asp Asn Gln Glu Asp Ala Glu Ala Ile Thr His Leu Phe Thr
                85                  90                  95

Asp Val Gln Asn Arg Tyr Thr Phe Ala Phe Gly Gly Asn Tyr Asp Arg
```

-continued

```
                100                 105                 110
Leu Glu Gln Leu Ala Gly Asn Leu Arg Glu Asn Ile Glu Leu Gly Asn
            115                 120                 125

Gly Pro Leu Glu Glu Ala Ile Ser Ala Leu Tyr Tyr Ser Thr Gly
        130                 135                 140

Gly Thr Gln Leu Pro Thr Leu Ala Arg Ser Phe Ile Ile Cys Ile Gln
145                 150                 155                 160

Met Ile Ser Glu Ala Ala Arg Phe Gln Tyr Ile Glu Gly Glu Met Arg
                165                 170                 175

Thr Arg Ile Arg Tyr Asn Arg Arg Ser
            180                 185

<210> SEQ ID NO 10
<211> LENGTH: 200
<212> TYPE: PRT
<213> ORGANISM: Ricinus communis

<400> SEQUENCE: 10

Met Ile Phe Pro Lys Gln Tyr Pro Ile Ile Asn Phe Thr Thr Ala Gly
  1               5                  10                  15

Ala Thr Val Gln Ser Tyr Thr Asn Phe Ile Arg Ala Val Arg Gly Arg
                 20                  25                  30

Leu Thr Thr Gly Ala Asp Val Arg His Glu Ile Pro Val Leu Pro Asn
             35                  40                  45

Arg Val Gly Leu Pro Ile Asn Gln Arg Phe Ile Leu Val Glu Leu Ser
         50                  55                  60

Asn His Ala Glu Leu Ser Val Thr Leu Ala Leu Asp Val Thr Asn Ala
 65                  70                  75                  80

Tyr Val Val Gly Tyr Arg Ala Gly Asn Ser Ala Tyr Phe Phe His Pro
                 85                  90                  95

Asp Asn Gln Glu Asp Ala Glu Ala Ile Thr His Leu Phe Thr Asp Val
            100                 105                 110

Gln Asn Arg Tyr Thr Phe Ala Phe Gly Gly Asn Tyr Asp Arg Leu Glu
        115                 120                 125

Gln Leu Ala Gly Asn Leu Arg Glu Asn Ile Glu Leu Gly Asn Gly Pro
    130                 135                 140

Leu Glu Glu Ala Ile Ser Ala Leu Tyr Tyr Ser Thr Gly Gly Thr
145                 150                 155                 160

Gln Leu Pro Thr Leu Ala Arg Ser Phe Ile Ile Cys Ile Gln Met Ile
                165                 170                 175

Ser Glu Ala Ala Arg Phe Gln Tyr Ile Glu Gly Glu Met Arg Thr Arg
            180                 185                 190

Ile Arg Tyr Asn Arg Arg Ser Ala
        195                 200

<210> SEQ ID NO 11
<211> LENGTH: 190
<212> TYPE: PRT
<213> ORGANISM: Ricinus communis

<400> SEQUENCE: 11

Met Ile Phe Pro Lys Gln Tyr Pro Ile Ile Asn Phe Thr Thr Ala Gly
  1               5                  10                  15

Ala Thr Val Gln Ser Tyr Thr Asn Phe Ile Arg Ala Val Arg Gly Arg
                 20                  25                  30

Leu Thr Val Leu Pro Asn Arg Val Gly Leu Pro Ile Asn Gln Arg Phe
```

```
                35                  40                  45
Ile Leu Val Glu Leu Ser Asn His Ala Glu Leu Ser Val Thr Leu Ala
            50                  55                  60

Leu Asp Val Thr Asn Ala Tyr Val Val Gly Tyr Arg Ala Gly Asn Ser
65                  70                  75                  80

Ala Tyr Phe Phe His Pro Asp Asn Gln Glu Asp Ala Glu Ala Ile Thr
                85                  90                  95

His Leu Phe Thr Asp Val Gln Asn Arg Tyr Thr Phe Ala Phe Gly Gly
            100                 105                 110

Asn Tyr Asp Arg Leu Glu Gln Leu Ala Gly Asn Leu Arg Glu Asn Ile
            115                 120                 125

Glu Leu Gly Asn Gly Pro Leu Glu Glu Ala Ile Ser Ala Leu Tyr Tyr
        130                 135                 140

Tyr Ser Thr Gly Gly Thr Gln Leu Pro Thr Leu Ala Arg Ser Phe Ile
145                 150                 155                 160

Ile Cys Ile Gln Met Ile Ser Glu Ala Ala Arg Phe Gln Tyr Ile Glu
                165                 170                 175

Gly Glu Met Arg Thr Arg Ile Arg Tyr Asn Arg Arg Ser Ala
            180                 185                 190

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:  RTA198
      primer for Nde I site.

<400> SEQUENCE: 12
gaattccata tgatcttccc aaagc                                         25

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: RTA198
      primer for stop codon and Sal I site.

<400> SEQUENCE: 13
gtcgacctag gatctacggt tgtatctaat tc                                 32

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Sense PCR
      oligonucleotide sequence.

<400> SEQUENCE: 14
ctgtcagagg tagattgact gtcttgccta acagagttgg                         40

<210> SEQ ID NO 15
<211> LENGTH: 40
<212> TYPE: DNA
<213> ORGANISM: Artificial Sequence
<220> FEATURE:
```

```
<223> OTHER INFORMATION: Description of Artificial Sequence:  Antisense
      PCR oligonucleotide sequence

<400> SEQUENCE: 15
ccaactctgt taggcaagac agtcaatcta cctctgacag                              40
```

RICIN TOXIN A-CHAIN FRAGMENT FOR USE AS A VACCINE

CROSS REFERENCE TO RELATED APPLICATIONS

This application is a continuation of U.S. application Ser. No. 10/083,336, filed 27 Feb. 2002, now U.S. Pat. No. 6,869,787, issued 22 Mar. 2005, which is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to ricin toxin. In particular, the present invention relates to ricin vaccines as well as methods of making and using thereof.

2. Description of the Related Art

Ricin is a very toxic protein obtained from the castor bean, *Ricinus communis, Euphorbiaceae*. Ricin is a heterodimer comprising an A chain and a B chain joined by a disulfide bond. Ricin A chain (RTA) is an N-glycosidase enzyme that irreversibly damages a specific adenine base from 28S rRNA. Once the rRNA has been damaged, the cell cannot make protein and will inevitably die (cytotoxicity). As RTA exhibits this type of destructive catalytic activity, RTA is commonly referred to as a type II ribosome inactivating protein (RIP). See Lord, et al. (1991) Semin. Cell Biol. 2(1):15-22. RTA has been coupled with a targeting moiety to selectively destroy target cells such as tumor cells. See U.S. Pat. Nos. 4,80,457; 4,962,188; and 4,689,401; see also Vitetta et al. (1993) Trends Pharmacol. Sci. 14:148-154 and Ghetie & Vitetta (1994) Cancer Drug Delivery 2:191-198.

The toxic consequences of ricin are due to the biological activity of RTA. Ricin B chain (RTB) binds the toxin to cell surface receptors and then RTA is transferred inside the cell where inhibition of ribosome activity occurs. The human lethal dose of ricin toxin is about 1 µg/kg. As highly purified ricin is commercially available, the use of ricin toxin in biological warfare and terrorism is highly possible and probable. Unfortunately, there is no effective antidote for toxic exposure to ricin. Thus, attempts have been made to provide vaccines against ricin intoxication.

Ricin vaccines have been prepared by isolating the natural toxin from castor beans, and treating the toxin with harsh chemicals, such as typically formaldehyde, to reduce the toxic activity. See Hewetson, et al. (1993) Vaccine 11(7):743-746; Griffiths, et al. (1995) Hum. Exp. Toxicol. 14(2):155-164; Griffiths, et al. (1999) Vaccine 17(20-21):2562-2568; and Yan, et al. (1996) Vaccine 14(11):1031-1038. These first generation vaccines are called "toxoid" vaccines as they are made directly from natural toxin itself. The current toxoid vaccine suffers from several important limitations that include: (1) the presence of both RTA and RTB; (2) the presence of trace amounts of active RTA and RTB; (3) the possibility that denatured toxoid could refold and, thereby, revert to the active form; (4) side-effects that arise from the presence of the harsh chemicals used in the vaccine formulation; (5) heterogeneity in the final vaccine product arising from the process of formaldehyde treatment; and (6) heterogeneity in the final vaccine resulting from the natural structural variations of ricin protein found in castor beans. See Despeyroux, et al. (2000) Anal. Biochem. 279(1):23-36.

The second generation ricin vaccines comprise wild-type (wt) RTA, but not RTB. See U.S. Pat. No. 5,453,271. Early efforts centered on isolating the whole toxin from castor beans, and then purifying RTA from RTB. Unfortunately, there are major problems associated with the use of natural or wt RTA as a vaccine such as: (1) heterogeneity at the level of protein composition (Despeyroux, et al. (2000) supra); (2) heterogeneity at the level of sugar composition (N-linked and/or o-linked carbohydrates covalently attached to the polypeptide backbone) (Despeyroux, et al. (2000) supra); (3) retention of naturally toxic N-glycosidase-rRNA enzymatic activity; (4) the poor solubility of isolated RTA in the absence of RTB, as evidenced by protein aggregation under physiological conditions; (5) rapid clearance circulation by the liver, thereby reducing the effectiveness of the vaccine (Wawrzynczak, et al. (1991) Int. J. Cancer 47:130-135); and (6) causing lesions of the liver and spleen.

Heterogeneity (variability) in a vaccine is undesirable as standardized and reproducible vaccine lots are necessary for regulatory compliance and approval. To reduce the heterogeneity of RTA vaccines, deglycosylated RTA (dgRTA) vaccines were produced. See International patent publication WO 00/53215. Unfortunately, dgRTA is still poorly soluble. Additionally, both dgRTA and wt recombinant RTA (rRTA) retain toxic N-glycosidase-rRNA enzymatic activity, which poses a safety risk. See Blakey, et al. (1987) Cancer Res. 47(4):947-952; Foxwell, et al. (1987) Biochim. Biophys. Acta. 923(1):59-65; Soler-Rodriguez, et al. (1992) Int. J. Immunopharmacol. 14(2):281-291; and Schindler, et al. (2001) Clin. Cancer Res. 7(2):255-258. Attempts at eliminating the toxic enzymatic activity of wt RTA gave rise to the third generation of ricin vaccines.

The third generation ricin vaccines are based on the active site of RTA that comprises the amino acid residues that interact directly with, or are within about five angstroms from, the bound ribosomal RNA substrate. Specifically, these mutant substitution RTA vaccines are based on recombinant DNA technology and substitute amino acids of wt RTA in order to reduce N-glycosidase-rRNA activity. See Ready, et al. (1991) Proteins 10(3):270-278; Kim, et al. (1992) Biochem. 31:3294-3296; Roberts, et al. (1992) Targeted Diag. Ther. 7:81-97; Frankel, et al. (1989) Mol. Cell. Biol. 9(2):415-420; and Gould, et al. (1991) Mol. Gen. Genet. 230(1-2):81-90.

Unfortunately, these mutant substitution RTA vaccines are problematic because unwanted changes often occur in the protein structure and render the protein unstable. Self-organization of the native RTA tertiary fold is optimized by the electrostatic charge balance of the active site cavity. See Olson (2001) Biophys. Chem. 91(3) 219-229. Thus, amino acid substitutions that alter the charge balance lead to structural reorganization coupled with a reduction in protein-fold stability. For example, disrupting the ion-pair between amino acid residues, Glu-177 and Arg-180, at the active site cavity by replacing the arginine with a histidine affects the global stability of the protein if the imidazole ring is deprotonated. See Day, et al. (1996) Biochem. 35(34): 11098-11103. The more stable form of mutant substitution RTA R180H, reduces the overall enzymatic activity about 500-fold, yet remains cytotoxic.

Another example of a failed substitution was mutant substitution RTA E177A. The x-ray crystallographic structure of RTA E177A demonstrates a remarkable rescue of electrostatic balance in the active site, achieved by the rotation of a proximal glutamic acid into the vacated space. See Kim, et al. (1992) supra. Despite the non-conservative substitution, the free energy of denaturation for RTA E177A was anticipated from modeling studies to be two-fold more favorable than the conservative replacement of mutant substitution RTA E177Q See Olson (2001) supra. In terms of expression levels, RTA E177Q is far less well behaved than wt RTA. See Ready, et al. (1991) supra. Additionally, both RTA E177A and RTA E177Q remain active enzymes, thereby indicating plasticity in obtaining the catalytic transition-state. See Schlossman, et al. (1989) Mol. Cell. Biol. 9(11):5012-5021; and Ready, et al. (1991) supra.

Thus, a need still exists for a vaccine that is stable, safe and effective against ricin intoxication.

SUMMARY OF THE INVENTION

The present invention generally relates to polypeptides related to ricin toxin A chain.

In some embodiments, the present invention relates to an isolated polypeptide or variant thereof comprising a polypeptide sequence having substantial identity to a wild type ricin A chain first globular domain sequence and which lacks detectable N-glycosidase-rRNA activity or exhibits reduced N-glycosidase-rRNA activity as compared to a control. The polypeptide may retain the functional integrity of the neutralizing immunological epitope of wild type ricin A chain. In some preferred embodiments, the polypeptide has a solubility that is greater than the solubility of wild type ricin A chain in aqueous solutions of physiological pH and ionic strength.

The wild type ricin A chain first globular domain sequence may be SEQ ID NO:2 or a variant thereof and the polypeptide of the present invention may comprise SEQ ID NO:3, SEQ ID NO:4, or variants thereof. The polypeptide of the present invention may be substantially identical to SEQ ID NO:3 or SEQ ID NO:4.

In some embodiments, the polypeptide of the present invention lacks a hydrophobic loop that corresponds to the hydrophobic loop of wild type ricin A chain. The polypeptide of the present invention may comprise at least one amino acid mutation, substitution, deletion, or a combination thereof.

The polypeptides of the present invention may be made by recombinant DNA techniques or by proteolytically cleaving the first globular domain and the second globular domain of ricin A chain and then purifying the first globular domain.

In other embodiments, the present invention relates to isolated polynucleotides that encode the polypeptides or variants of the present invention.

In some embodiments, the present invention relates to antibodies raised against the polypeptides or variants of the present invention. In some embodiments, the antibody is a neutralizing antibody that is capable of neutralizing ricin, ricin A chain, or both.

In some embodiments, the present invention relates to a pharmaceutical composition comprising at least one polypeptide or variant of the present invention, or at least one polynucleotide of the present invention or at least one antibody of the present invention a pharmaceutically acceptable vehicle. The pharmaceutical composition may further comprise an adjuvant. The pharmaceutical composition may be capable of eliciting an immune response when administered to a subject. The immune response may be a protective immune response against ricin intoxication.

The present invention also relates to vaccines comprising an immunogenic amount of at least one polypeptide or variant of the present invention.

In some embodiments, the present invention relates to a method of inducing an immune response in a subject which comprises administering to the subject at least one immunogenic amount of the polypeptide or variant of the present invention. Preferably, the subject is mammalian, more preferably, the subject is human. The method may further comprise administering to the subject at least one booster dose.

In some embodiments, the present invention relates to a method of providing passive immunity against ricin intoxication in a subject comprising administering to the subject a therapeutically effective amount of at least one antibody raised against the polypeptides or variants of the present invention.

In other embodiments, the present invention relates to a method of treating or preventing ricin intoxication in a subject comprising administering to the subject an immunogenic amount of the polypeptide or variant of the present invention, or administering to the subject a therapeutically effective amount of an antibody raised against the polypeptide or variant of the present invention.

In some embodiments the present invention relates to kits comprising the polypeptides or variants of the present invention, or antibodies raised against the polypeptides or variants of the present invention, or polynucleotides of the present invention packaged together with instructions for use. The kits may further comprise diagnostic reagents such as labeling compounds for detecting the presence of ricin toxin or for diagnosing exposure of a subject to ricin. The kits may comprise drug delivery devices for administering the compositions of the present invention to a subject.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

The present invention provides polypeptides derived from native or wt RTA amino acid sequences, such as the amino acid sequence set forth in SEQ ID NO:1 (SwissProt accession no. P02879), for use in compositions and methods for treating or preventing ricin intoxication in a subject.

The structure of RTA comprises two globular domains according to a widely accepted method of evaluating protein secondary structure elements and packing called PDBSum, a web-based database of summaries and analyses of all PDB structures. See Laskowski R A, et al. (1997) Trends Biochem. Sci. 22:488-490. The first globular domain of RTA comprises amino acid residues from about 1 to about 179 (counting from the amino terminus) of native RTA which is set forth in SEQ ID NO:2. The second globular domain of RTA comprises amino acid residues from about position 180 to about 267 of native RTA. The second globular domain of RTA is the part that mainly interfaces with RTB.

Detailed computer-aided structural models of RTA were constructed using InsightII Biopolymer, Discover, and Delphi programs which are available from Accelrys Inc. (San Diego, Calif.), and the program GRASP developed by B. Honig of Columbia University (New York, N.Y.). Starting structures for these models included: (A) the three-dimensional crystal structures of ricin toxin, as well as natural RTA and RTB, and wt rRTA (Villafranca, et al. (1981) J. Biol. Chem. 256(2):554-556; Montfort, et al. (1987) J. Biol. Chem. 262(11):5398-5403; Katzin, et al. (1991) Proteins 10(3):251-259; Rutenber, et al. (1991) Proteins 10(3):240-250; and Weston, et al. (1994) J. Mol. Biol. 244(4):410-422, which are herein incorporated by reference); (B) the three-dimensional crystal structures of several ribosome inactivating proteins (RIPs) related to RTA, including pokeweed antiviral protein (PAP) (Monzingo, et al. (1992) J. Mol. Biol. 277(4): 1136-1145, which is herein incorporated by reference); and (C) published computer-aided theoretical models of RTA in solution (Olson (1997) Proteins 27(1):80-95; Lebeda (1997) Int. J. Biol. Macromol. 24(1):19-26; and Olson (1999) COMPUTATIONAL CHEMISTRY: REVIEWS OF CURRENT TRENDS. J. Leszczynski. Singapore, World Scientific Publishing C. Pte. Ltd. 4:153-190, which are herein incorporated by reference). The computer-aided models were used to design and develop the polypeptides of the present invention for use as safe and efficacious ricin vaccines.

Figure 1:
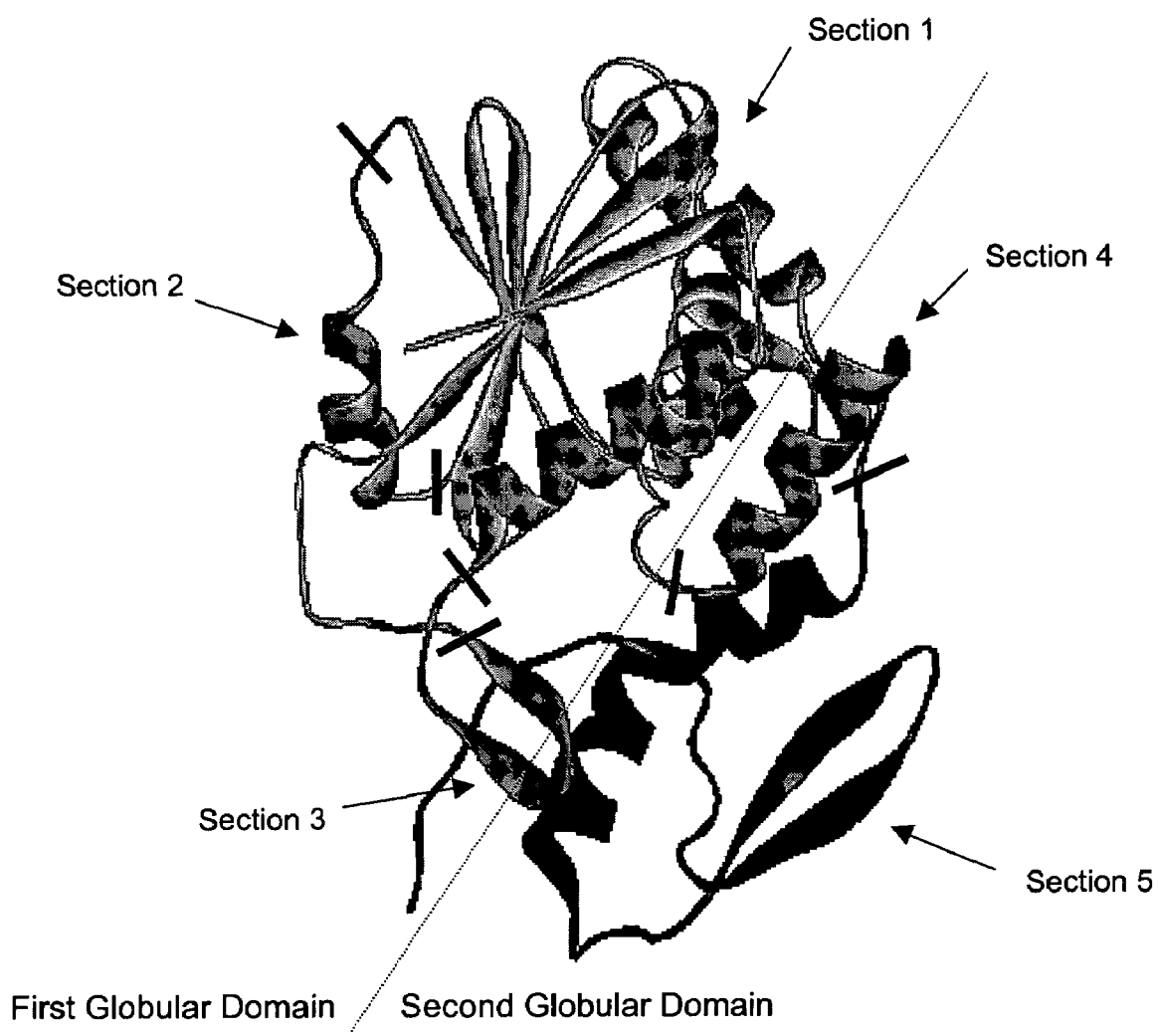
FIG. 1 is a ribbon diagram of wt RTA.

Analysis of computer-aided models suggested that native RTA could be converted into a much smaller, stably folded vaccine scaffold by careful placement of a break in the polypeptide backbone within a specific coiled region near the start of the second globular domain of RTA. This specific coiled region is referred to as the "linker region" of RTA and comprises amino acid residues from about position 195 to about 202 of native RTA. A ribbon diagram depicting the three-dimensional topology of RTA derived from the solved crystal structure is shown in FIG. 1. See Weston, et al. (1994) supra, which is herein incorporated by reference. The first globular domain comprises sections 1, 2, and 3 and the second globular domain comprises sections 4 and 5. The neutralizing immunogenic epitope, section 2, is believed to be the amino acid residues from about position 95 to about 110 of native RTA. See Aboud-Pirak, et al. (1993) Med. Def. Biosci. Rev., Baltimore, Md., U.S. Army Medical Research and Materiel Command, which is herein incorporated by reference. Based on structural analysis and protein chemistry, the first globular domain was determined to relate to immunogenicity and the second globular domain was determined to include the hydrophobic interfacial region that interacts directly with RTB.

The aqueous solubility of native RTA was determined to be limited by the absence of RTB. Moreover, major structural changes were identified that could be made in native RTA to overcome limited solubility by optimizing solute-solvent interactions. The significant changes described herein were surprisingly successful as significant changes to a polypeptide sequence usually results in an unfolded protein and, therefore, loss of utility as a biological therapeutic. Specifically, as disclosed herein, the engineered polypeptides do not retain any natural catalytic activity of RTA. Additionally, the engineered polypeptides retained the favorable thermodynamic equilibrium between folded and unfolded RTA. Most surprisingly, the functional integrity of the neutralizing immunological epitope of RTA was retained in the engineered polypeptides. Therefore, the present invention provides polypeptides that: (1) do not retain any natural catalytic activity of RTA; (2) retain the favorable thermodynamic equilibrium between folded and unfolded RTA; (3) retain the functional integrity of the neutralizing immunological epitope of RTA; or (4) a combination thereof.

As shown in the Examples below, significant changes in the linker region of wt RTA provided polypeptides having reduced surface hydrophobicity (increased solubility in aqueous solutions of physiological pH and ionic strength) or a reduced ability to form aggregates as well as reduced N-glycosidase-rRNA activity, if any, as compared to wt RTA. In particular, the engineered polypeptides that lack most of the second globular domain of RTA. Specifically, the second globular domain was deleted at position 198 of RTA since the second residue following the cleavage site is a proline (residue 200), and this residue was thought to be restrictive in the torsional backbone of the deleted domain.

Thus, the polypeptides of the present invention comprise at least one amino acid mutation, substitution, deletion, or a combination thereof, in the linker region of RTA. The polypeptides of the present invention comprise an amino acid sequence that has substantial identity to amino acid residues from about position 1 to about 210, preferably about 1 to about 202 of wt RTA, more preferably about 1 to about 198. In preferred embodiments, the polypeptides of the present invention comprise an amino acid sequence that has a substantial identity to amino acid residues from position 1 to 198 of wt RTA.

Further, as disclosed herein, amino acid residues in the first globular domain that do not change its overall stability and do not change the neutralizing immunogenic epitope of wt RTA may be removed. Specifically, deletion of amino acid residues between positions 33 and 44 of wt RTA still provided a stable polypeptide that retained immunogenicity.

Thus, the polypeptides of the present invention comprise at least one amino acid mutation, substitution, deletion, or a combination thereof, in the linker region and in the first globular domain of wt RTA. The polypeptides of the present invention comprise an amino acid sequence that has substantial identity to amino acid residues from position 1 to about 210, preferably about 1 to about 200, more preferably about 1 to about 198 of wt RTA and include at least one amino acid mutation, substitution, deletion, or a combination thereof, in the first globular domain, preferably in the loop region, more preferably from about position 33 to about 44 of wt RTA. In preferred embodiments, the amino acid mutation, substitution, deletion, or a combination thereof, is a deletion of amino acid residues from about position 34 to about 43 of wt RTA.

The polypeptides of the present invention are stable, non-toxic, and capable of eliciting an immune response in a subject. Thus, the polypeptides of the present invention may be used to prevent or treat systemic side effects of locally administered ricin toxin. In preferred embodiments, the polypeptides of the present invention are capable providing a protective immune response in a subject. Preferably, the subject is mammalian, more preferably, the subject is human. As used herein, an "immune response" refers to a humoral or cellular response caused by exposure to an antigenic substance. Thus, an immune response against ricin or "ricin immune response" refers to a humoral or cellular response in a subject that is caused by exposing the subject to an antigenic substance such as polypeptides of the present invention. A "protective immune response" against ricin refers to humoral immune responses, cellular immune responses, or both, that are sufficient to inhibit or prevent ricin intoxication in a subject.

In some embodiments, the polypeptides of the present invention comprise at least one amino acid mutation, substitution, deletion, or a combination thereof, in the linker region of the second globular domain of LTA such as the following:

A. RTA198 (designated from the protein amino terminus to the protein carboxyl terminus):

(SEQ ID NO:3)
IFPKQYPIINFTTAGATVQSYTNFIRAVRGRLTTGADVRHEIPVLPNRVG

LPINQRFILVELSNHAELSVTLALDVTNAYVVGYRAGNSAYFFHPDNQED

AEAITHLFTDVQNRYTFAFGGNYDRLEQLAGNLRENIELGNGPLEEAISA

LYYYSTGGTQLPTLARSFIICIQMISEAARFQYIEGEMRTRIRYNRRS;
and

B. RTA1-33/44-198 (designated from the protein amino terminus to the protein carboxyl-terminus) The bold type face of SEQ ID NO:4 indicates the position where the hydrophobic loop would be when compared with wt RTA:

(SEQ ID NO:4)
IFPKQYPIINFTTAGATVQSYTNFIRAVRGRLTVLPNRVGLPINQRFILV

ELSNHAELSVTLALDVTNAYVVGYRAGNSAYFFHPDNQEDAEAITHLFTD

VQNRYTFAFGGNYDRLEQLAGNLRENIELGNGPLEEAISALYYYSTGGTQ

LPTLARSFIICIQMISEAARFQYIEGEMRTRIRYNRRS

The polypeptides of the present invention need not be identical to those exemplified herein so long as the subject polypeptides are able to induce an immune response against RTA, ricin, or both. Thus, as used herein "variants" of the polypeptides of the present invention refer to polypeptides having insignificant changes such as a methionine as the first amino acid residue at the amino terminus, conservative amino acid substitutions, deletion of or insertion of up to about 10 amino acid residues in the linker or loop region of wt RTA, and co-translational or post-translational surface modifications such as the addition of covalently attached sugars or lipids. Insignificant changes refer to modifications in the amino acid sequence of a given polypeptide that do not change the solubility, N-glycosidase-rRNA activity, or immunogenicity of the polypeptide.

Examples of such variants include:

(SEQ ID NO:5)
a. MIFPKQYPIINFTTAGATVQSYTNFIRAVRGRLTTGADVRHEIPVLP
NRVGLPTNQRFILVELSNHAELSVTLALDVTNAYVVGYRAGNSAYFF
HPDNQEDAEAITHLFTDVQNRYTFAFGGNYDRLEQLAGNLRENIELG
NGPLEEAISALYYYSTGGTQLPTLARSFIICIQMISEAARFQYIEGE
MRTRIRYNRRS (SEQ ID NO:6)
b. MIFPKQYPIINFTTAGATVQSYTNFIRAVRGRLTVLPNRVGLPINQR
FILVELSNHAELSVTLALDVTNAYVVGYRAGNSAYFFHPDNQEDAEA
ITHLFTDVQNRYTFAFGGNYDRLEQLAGNLRENIELGNGPLEEAISA
LYYYSTGGTQLPTLARSFIICIQMISEAARFQYTEGEMRTRIRYNRR
S (SEQ ID NO:7)
c. MVPKQYPIINFTTAGATVQSYTNFIRAVRGRLTTGADVRHEIPVLPN
RVGLPINQRFILVELSNHAELSVTLALDVTNAYVVGYRAGNSAYFFH
PDNQEDAEAITHLFTDVQNRYTFAFGGNYDRLEQLAGNLRENIELGN
GPLEEAISALYYYSTGGTQLPTLARSFIICIQMISEAARFQYIEGEM
RTRIRYNRRS (SEQ ID NO:8)
d. MVPKQYPIINFTTAGATVQSYTNFIRAVRGRLTVLPNRVGLPINQRF
ILVELSNHAELSVTLALDVTNAYVVGYPAGNSAYFFHPDNQEDAEAI
THLFTDVQNRYTFAFGGNYDRLEQLAGNLRENIELGNGPLEEAISAL
YYYSTGGTQLPTLARSFIICIQMISEAARFQYIEGEMRTRIRYNRRS

-continued (SEQ ID NO:9)
e. IFPKQYPIINFTTAGATVQSYTNFIRAVRGRLTNRVGLPINQRFILV
ELSNHAELSVTLALDVTNAYVVGYRAGNSAYFFHPDNQEDAEAITHL
FTDVQNRYTFAFGGNYDRLEQLAGNLRENIELGNGPLEEAISALYYY
STGGTQLPTLARSFIICIQMISEAARFQYIEGEMRTRIRYNRRS (SEQ ID NO:10)
f. MIFPKQYPIINFTTAGATVQSYTNFIRAVRGRLTTGADVRHEIPVLP
NRVGLPINQRFILVELSNHAELSVTLALDVTNAYVVGYRAGNSAYFF
HPDNQEDAEAITHLFTDVQNRYTFAFGGNYDRLEQLAGNLRENIELG
NGPLEEAISALYYYSTGGTQLPTLARSFIICIQMISEAARFQYIEGE
MRTRIRYNRRSA (SEQ ID NO:11)
g. MIFPKQYPIINFTTAGATVQSYTNFIPAVRGRLTVLPNRVGLPINQR
FILVELSNHAELSVTLALDVTNAYVVGYPAGNSAYFFHPDNQEDAEA
ITHLFTDVQNRYTFAFGGNYDRLEQLAGNLRENIELGNGPLEEAISA
LYYYSTGGTQLPTLARSFIICIQMISEAARFQYIEGEMRTRIRYNRR
SA The polypeptides of the present invention may also be modified to provide a variety of desired attributes, e.g., improved pharmacological characteristics, while increasing or at least retaining substantially all of the immunological activity of the RTA. By using conventional methods in the art, one of ordinary skill will be readily able to make a variety of polypeptides having mutated linker regions and then screen the polypeptides for stability, toxicity, and immunogenicity according to the present invention.

Additionally, single amino acid substitutions, deletions, or insertions can be used to determine which residues are relatively insensitive to modification. Amino acid substitutions are preferably made between relatively neutral moieties, such as alanine, glycine, proline, and the like. Substitutions with different amino acids, of either D or L isomeric forms, or amino acid mimetics can be made. The number and types of substitutions, deletions, and insertions depend on the functional attributes that are sought such as hydrophobicity, immunogenicity, three-dimensional structure, and the like.

An "amino acid mimetic" as used herein refers to a moiety other than a naturally occurring amino acid residue that conformationally and functionally serves as a suitable substitute for an amino acid residue in a polypeptide of the present invention. A moiety is a suitable substitute for an amino acid residue if it does not interfere with the ability of the peptide to elicit an immune response against ricin. Examples of amino acid mimetics include cyclohexylalanine, 3-cyclohexylpropionic acid, L-adamantyl alanine, adamantylacetic acid, and the like. See e.g. Morgan and Gainor, (1989) Ann. Repts. Med. Chem. 24:243-252.

Individual amino acid residues may be incorporated in the polypeptides of the present invention with peptide bonds or peptide bond mimetics. A peptide bond mimetic include peptide backbone modifications of the amide nitrogen, the α-carbon, amide carbonyl, complete replacement of the amide bond, extensions, deletions or backbone crosslinks. See e.g. Spatola (1983) Chemistry and Biochemistry of Amino Acids, Peptides and Proteins, Vol. VII, Weinstein ed. The polypeptides of the present invention may include an additional methionine as the first amino acid residue on the protein amino terminus. The polypeptides may be truncated by up to about ten (10) amino acid residues from the carboxyl terminus of RTA198, RTA1-33/44-198, or the like. Similarly, up to about ten (10) amino acid residues from wt RTA bordering the hydrophobic loop, amino acid residues at about position 34 to about 43 may be deleted. Additionally, co-translational or post-translational surface modifications, such as the addition of covalently attached sugars or lipids, may be made to the polypeptides of the present invention.

In preferred embodiments, the polypeptides of the present invention have a substantial sequence identity to the amino acid sequence set forth in SEQ ID NOs:2, 3, and 4. As used herein "sequence identity" means that two sequences are identical over a window of comparison. The percentage of sequence identity is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

The structural models and conclusions deduced for RTA may be applied to the solved three-dimensional structure of related proteins, such as other RIPs. This could be done by a structure-structure alignment that minimizes the root-mean-square-deviation of atomic coordinates among the aligned structure (for example, optimal superposition of the position of all atoms, or the protein backbone atoms or the alpha-carbon atoms). Such methods are now largely automated, see for example, the homology module of Insight II (Accelrys, Inc., San Diego, Calif.); the Combinatorial Extension (CE) of the optimal path method (Shindyalov and Bourne (1998) Protein Engineering 11:739-747); and the Vector Alignment Search Tool (VAST) (Gibrat, Madej and Bryant (1996) Current Opinion in Structural Biology 6:377-385), which are incorporated herein by reference. Preferably, the amino acid residues in corresponding positions among aligned structures are identical or differ only by "conservative amino acid substitutions".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan).

Additionally, the structural information and conclusions deduced for RTA could be applied to other protein sequences, such as other RIPs, by an alignment of known structures (e.g., RTA and PAP), and then a subsequent alignment of the unknown structure with the structurally aligned sequences. Such methods are now largely automated. See e.g., SAS program suite of Milbum, D., et al. (1998) Protein Engineering 11:855-859, which is herein incorporated by reference; see also Homologous Structure Alignment Database (HOMSTRAD). Mizuguchi, Deane, Blundell, and Overignton (1998) Protein Science 7:2469-2471 world wide web address-cryst.bioc.cam.ac.uk/~homstrad/), which is herein incorporated by reference.

The polypeptides of the present invention may be made by conventional methods known in the art. The polypeptides of the present invention may be manually or synthetically synthesized using conventional methods and devices known in the art. See e.g., Stewart and Young (1984) Solid Phase Peptide Synthesis, 2 ed. Pierce, Rockford, Ill., which is herein incorporated by reference. Ricin or RTA may be obtained by conventional methods. See U.S. Pat. No. 5,547,867, which is herein incorporated by reference. The ricin or RTA may then be exposed to proteolytic enzymes that cleave the amino acid residues to obtain polypeptides of the present invention. Ricin and RTA may be purified from natural sources using conventional protein purification techniques such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and see e.g., Scopes (1982) Protein Purification, Springer-Verlag, NY, which are herein incorporated by reference.

Prior art methods for purifying RTA rely upon the separation of RTA and RTB by disulfide reduction and subsequence lectin binding, or affinity chromatography with specialized affinity resins. See Fulton et al. (1986) J. Biol. Chem. 261: 5314-5319 and Emmanuel et al. (1988) Anal. Biochem. 173: 134-141, which are herein incorporated by reference. Since the biophysical properties of the polypeptides, i.e. isoelectric points, of the present invention are different from wt RTA, the polypeptides of the present invention may be purified without the use of sulfhydryl reduction or costly, specialized affinity resins. Specifically, conventional ion-exchange chromatography based upon the isoelectric points of the polypeptides may be used to purify the polypeptides of the present invention.

In preferred embodiments, the polypeptides of the present invention are substantially purified. As used herein, a "substantially purified" compound refers to a compound that is removed from its natural environment and is at least about 60% free, preferably about 75% free, and most preferably about 90% free from other macromolecular components with which the compound is naturally associated.

Alternatively, the polypeptides of the present invention may be made by conventional recombinant DNA techniques such as those disclosed in the Examples below. Thus, the present invention provides polynucleotides that encode the polypeptides of the present invention. In preferred embodiments, the polynucleotides are isolated. As used herein "isolated polynucleotides" refers to polynucleotides that are in an environment different from that in which the polynucleotide naturally occurs.

A polynucleotide that encodes a polypeptide having substantial identity to either SEQ ID NO:2 or SEQ ID NO:3 can be made by introducing one or more nucleotide substitutions, insertions, or deletions into the nucleotide sequence that encodes SEQ ID NO:1, SEQ ID NO:2, or SEQ ID NO:3 such that one or more amino acid substitutions, insertions, or deletions are introduced into the encoded polypeptide. Mutations can be introduced by standard techniques, such as site-directed mutagenesis and PCR-mediated mutagenesis.

A polynucleotide encoding a polypeptide of the present invention is then inserted in to a vector such as a cloning vector or an expression vector. An expression vector allows the polypeptide to be expressed when present in a host. Either the expression vector or the host may comprise the regulatory sequences necessary for expression of the polypeptide. Where the regulatory sequences are within the expression vector, the regulatory sequences are operatively linked to the sequence encoding the polypeptide. As used herein, "operably linked" means that the nucleotide sequence of interest is linked to at least one regulatory sequence in a manner that allows the polypeptide to be expressed in an in vitro transcription/translation system or in a host cell. Regulatory sequences include promoters, enhancers and other expression control elements (e.g., polyadenylation signals). See e.g., Goeddel (1990) Gene Expression Technology: Methods in Enzymology, Academic Press, San Diego, Calif., which is herein incorporated by reference.

It will be appreciated by those skilled in the art that the design of the expression vector can depend on such factors as the choice of the host cell to be transformed, the desired expression levels of the polypeptide, the compatibility of the host cell and the expressed polypeptide, and the like.

The vectors can be designed for expressing the polypeptides of the present invention of in prokaryotic or eukaryotic host cells such as bacterial cells, insect cells, plant cells, yeast cells, or mammalian cells. In preferred embodiments, the host cells are bacterial cells. Suitable host cells are discussed further in Goeddel supra; Baldari, et al. (1987) EMBO J. 6:229-234; Kurjan and Herskowitz (1982) Cell 30:933-943; Schultz, et al. (1987) Gene 54:113-123; Smith, et al. (1983) Mol. Cell Biol. 3:2156-2165; Lucklow and Summers (1989) Virology 170:31-39; Seed (1987) Nature 329:840; Kaufman, et al. (1987) EMBO J. 6:187-6195; Sambrook, et al. (2000) MOLECULAR CLONING: A LABORATORY MANUAL. Cold Spring Harbor Laboratory, Cold Spring Harbor Laboratory Press, Cold Spring Harbor, N.Y.; and those available from Invitrogen Corporation, San Diego, Calif., such as pYES2 and picZ, all of which are herein incorporated by reference.

Thus, the present invention also provides host cells comprising polynucleotides that encode the polypeptides of the present invention. Host cells include the progeny or potential progeny of the primary cell in which the polynucleotide was introduced. Because certain modifications may occur in succeeding generations due to either mutation or environmental influences, such progeny may not, in fact, be identical to the parent cell, but are still included within the scope and meaning of host cell.

A polypeptide of the present invention may be used to prepare antibodies against ricin by immunizing a suitable subject, e.g., rabbit, goat, mouse or other mammal with the polypeptide by conventional methods known in the art. Large quantities of neutralizing antibodies could be generated and then used as an antidote for ricin intoxication. See Lemley, et al. (1994) Hybridoma 13(5):417-427 and U.S. Pat. No. 5,626,844, which are herein incorporated by reference. The antibodies raised against the polypeptides of the present invention may be used to prevent or treat systemic side effects of locally administered ricin toxin. Thus, the present invention also provides antibodies that are raised against or derived from the polypeptides of the present invention, and methods of using thereof.

Antibodies of the present invention may be produced by conventional methods known in the art. See e.g., Coligan (1991) CURRENT PROTOCOLS IN IMMUNOLOGY. Wiley/Greene, NY; and Harlow and Lane (1989) ANTIBODIES: A LABORATORY MANUAL, Cold Spring Harbor Press, NY; Stites, et al. (1986) BASIC AND CLINICAL IMMUNOLOGY. 4th ed. Lange Medical Publications, Los Altos, Calif.; Goding (1986) MONOCLONAL ANTIBODIES: PRINCIPLES AND PRACTICE. 2d ed. Academic Press, New York, N.Y.; and Kohler and Milstein (1975) Nature 256:495-497, which are herein incorporated by reference. Therapeutic antibodies may be produced specifically for clinical use in humans by conventional methods known in the art. See Chadd, H. E. and S. M. Chamow (2001) Curr. Opin. Biotechnol. 12:188-194 and references therein, all of which are herein incorporated by reference. The present invention has the advantage of allowing safe exposure of subjects, such as humans, to the RTA neutralizing epitope. Thus, the present invention allows for the safe in vivo production of RTA antibodies directly subjects.

As used herein, "antibody" refers to immunoglobulin molecules and immunologically active portions that comprise an antigen binding site which specifically binds an antigen, such as ricin. Examples of immunologically active portions of immunoglobulin molecules include F(ab) and F(ab')$_2$ fragments which may be generated by treating the antibody with an enzyme such as pepsin. Polyclonal and monoclonal antibodies against the polypeptides of the present invention may be made by conventional methods known in the art.

The polypeptides, polynucleotides, or antibodies of the present invention may be administered, preferably in the form of pharmaceutical compositions, to a subject. Preferably the subject is mammalian, more preferably, the subject is human. Preferred pharmaceutical compositions are those comprising at least one immunogenic composition against ricin, RTA, or both, in an immunogenic amount or a therapeutically effective amount, and a pharmaceutically acceptable vehicle. The immunogenic composition may be an active immunizing agent, such as a polypeptide of the present invention, or a passive immunizing agent, such as an antibody raised against the polypeptide of the present invention. The immunogenic composition may elicit an immune response that need not be protective or the immunogenic composition may provide passive immunity. A vaccine elicits a local or systemic immune response that is protective against subsequent challenge by the immunizing agent such as the polypeptides of the present invention, or an immunologically cross-reactive agent, such as ricin. Conventional methods in the art may be used to determine the feasibility of using the polypeptides of the present invention as vaccines against ricin intoxication. Accordingly, as used herein, an "immunogenic composition" can refer to vaccines as well as antibodies. A protective immune response may be complete or partial, i.e. a reduction in symptoms as compared with an unvaccinated mammal.

Thus, the present invention provides immunogenic compositions comprising the polypeptides or the antibodies of the present invention that may be used to immunize a subject against ricin by methods known in the art. See U.S. Pat. No. 5,453,271, which is herein incorporated by reference. As used herein, an "immunogenic amount" is an amount that is sufficient to elicit an immune response in a subject and depends on a variety of factors such as the immunogenicity of the polypeptide, the manner of administration, the general state of health of the subject, and the like. The typical immunogenic amounts for initial and boosting immunization for therapeutic or prophylactic administration ranges from about 0.01 mg to about 0.1 mg per about 65-70 kg body weight of a subject. For example, the typical immunogenic amount for initial and boosting immunization for therapeutic or prophylactic administration for a human subject ranges from about 0.01 mg to about 0.1 mg. Examples of suitable immunization protocols include initial immunization injections at time 0 and 4 or initial immunization injections at 0, 4, and 8 weeks, which initial immunization injections may be followed by further booster injections at 1 or 2 years.

As used herein, a "therapeutically effective amount" refers to an amount of a polypeptide, a polynucleotide, or an antibody that may be used to treat, prevent, or inhibit ricin intoxication in a subject as compared to a control. Again, the skilled artisan will appreciate that certain factors may influence the dosage required to effectively treat a subject, including the severity of ricin exposure, previous treatments, the general health and age of the subject, and the like. A therapeutically effective amount may be readily determined by conventional methods known in the art. It should be noted that treatment of a subject with a therapeutically effective amount of a polypeptide, a polynucleotide, or an antibody of the present invention can include a single treatment or, preferably, can include a series of treatments.

The pharmaceutical compositions may include an adjuvant. As used herein, an "adjuvant" refers to any substance which, when administered with or before the polypeptide, polynucleotide, or antibody of the present invention, aids the polypeptide, polynucleotide, or antibody in its mechanism of action. Thus, an adjuvant in a vaccine is a substance that aids the immunogenic composition in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxy-phosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by conventional methods in the art.

The compositions of the present invention may be administered to a subject by any suitable route including oral, transdermal, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular polypeptide, polynucleotide, or antibody used.

As used herein, a "pharmaceutically acceptable vehicle" or "pharmaceutically acceptable carrier" refers to and includes any and all solvents, dispersion media, coatings, antibacterial and antifungal agents, isotonic and absorption delaying agents, and the like, that are compatible with pharmaceutical administration. Pharmaceutically acceptable vehicles include those known in the art. See e.g. REMINGTON: THE SCIENCE AND PRACTICE OF PHARMACY. $20^{th}$ ed. (2000) Lippincott Williams & Wilkins. Baltimore, Md., which is herein incorporated by reference.

The pharmaceutical compositions of the present invention may be provided in dosage unit forms. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals. For example, one may determine the lethal dose of toxin, $LCt_{50}$ (the dose expressed as concentration of toxin x exposure time that is lethal to 50% of the population) or the $LD_{50}$ (the dose lethal to 50% of the population), and the $ED_{50}$ (the dose therapeutically effective in 50% of the population) by conventional methods in the art. The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The present invention also provides polypeptides, polynucleotides, antibodies, or compositions of the present invention may be provided in kits along with instructions for use. A kit comprising a pharmaceutical composition may include the pharmaceutical composition as a single dose or multiple doses. The kit may include a device for delivering the pharmaceutical composition. The device may be a multi-chambered syringe for intramuscular delivery, a microneedle or set of microneedle arrays for transdermal delivery, a small balloon for intranasal delivery, or a small aerosol generating device for delivery by inhalation.

Ricin exposure is presently detected by medical history and symptoms, and is confirmed by antibody- or activity-based measurements of ricin in bodily fluids. Ricin detection or medical diagnosis of ricin exposure, therefore, may based upon immunoassays utilizing the antibodies or polypeptides of the present invention or combinations thereof. Since a subject may be safely exposed to the polypeptides of the present invention, exposure to ricin may be determined by detecting RTA antibodies in a subject in vivo. Additionally, as the polypeptides of the present invention are relatively nontoxic and safe, immunoassays utilizing the polypeptides of the present invention for detecting antibodies against ricin would be also be safe. Thus, the present invention provides diagnostic assays for detecting ricin toxin, exposure to ricin, or both. The diagnostic assays may comprise the polypeptides of the present invention, antibodies of the present invention, or a combination thereof. The diagnostic assays may be provided in the form of kits that may be used outside of a laboratory setting, such as in the field.

As disclosed herein, the polypeptides of the present invention are fundamentally superior as immunogenic compositions such as ricin vaccines as compared ricin toxoid, wt RTAs, dgRTAs, and mutant substitution RTAs as the polypeptides do not include RTB, and lack detectable N-glycosidase-rRNA activity or exhibit reduced N-glycosidase-rRNA activity as compared to controls. As used herein, "detectable" N-glycosidase-rRNA activity refers to N-glycosidase-rRNA activity that may be detected by assays conventional in the art. See Hale (2001) Pharmacol. & Toxicol. 88:255-260, and Langer, M. M. et al. (1996) Anal. Biochem. 243:150-153, both of which are herein incorporated by reference. These conventional assays routinely detect the ribosome inactivating activity of native RTA at toxin concentrations of 0.1 to 0.5 nM. Thus, the polypeptides of the present invention that lack detectable N-glycosidase-rRNA activity refers to polypeptides that do not exhibit ribosome inactivating activity at concentrations of less than about 0.5 nM, preferably, less than about 0.1 nM.

The polypeptides of the present invention have an aqueous solubility that is greater than the aqueous solubility of wt RTA as evidenced by high expression yields in the soluble fraction and by the absence of protein aggregation or precipitation upon storage in physiological saline solutions. A direct comparison of dgRTA and polypeptides of the present invention was made using standard methods of SDS-PAGE and isoelectric focusing. Each method showed evidence of higher molecular weight species, indicative of aggregation, in the dgRTA samples that were absent from samples of the polypeptides of this invention. Additionally, the polypeptides of the present invention are more homogenous than dgRTA as the polypeptides may be consistently expressed and substantially purified as explained in Examples 1 and 2 and evidenced by the SDS-PAGEs in FIGS. 2 and 3.

The following Examples are intended to illustrate, but not to limit the present invention.

EXAMPLE 1

Construction and Analysis of RTA198

A. DNA Cloning, Sequencing, and Expression of RTA198

DNA cloning and sequencing was conducted using conventional methods in the art. See Sambrook, et al. (2000) supra, which is herein incorporated by reference. Cloning was based upon the published polypeptide sequence of RTA (SEQ ID NO:1, SwissProt accession number P07829). See Lamb, et al. (1985) Eur. J. Biochem. 148(2):265-270; and Roberts, et al. (1992) supra, which are herein incorporated by reference.

To make the polynucleotide that encodes RTA198, a "stop codon" was incorporated after the codon for serine 198 in wt RTA. Mutagenesis to introduce the stop codon was done using a QuickChange kit commercially available from Stratagene (La Jolla, Calif.) based upon the polymerase chain reaction method. Briefly, a BamH 1 endonuclease cleavage site was replaced with a site for Nde I at the 5' end of the RTA gene using the following primer: 5' GAA TTC CAT ATG ATC TTC CCA AAG C 3' (SEQ ID NO:12). Additionally, a stop codon and a Sal I restriction endonuclease cleavage site were introduced by use of the following primer: 5' GTC GAC CTA GGA TCT ACG GTT GTA TCT AAT TC 3' (SEQ ID NO:13). The reaction mixture, comprising RTA DNA template, PCR primer pairs, pfu DNA polymerase and dNTP, was subjected to PCR as outlined in the commercial kit (Stratagene, La Jolla, Calif.). Template DNA is then eliminated by incubating at 37° C. for 1 hour with Dpn I restriction endonuclease. A 1 µl sample of the PCR mixture containing the mutated polynucleotide was used to transform E. coli XL1-Blue competent E. coli cells (Stratagene, La Jolla, Calif.). Mutagenesis was conducted under contract by Clinical Research Management (Frederick, Md.). The resultant mutated polynucleotide was purified using a commercial Miniprep kit (Qiagen, Valencia, Calif.) and sequenced using conventional methods to confirm that only the desired changes were made.

The DNA products were purified, ligated to a commercial pET-24 expression vector based upon the T7 promoter system of Studier, et al. (1990) Methods Enzymol. 185:60-89, which is herein incorporated by reference, and then used to transform competent E. coli BL21 DE3 cells (Invitrogen, Calif.). Plasmid DNA was purified by conventional methods in the art.

B. Expression of RTA198

The transformed E. coli BL 21 cells were cultured in Terrific Broth (TB; a standard bacterial cell culture medium comprising 12 g/L tryptone, 24 g/L yeast extract, 0.4% (v/v) glycerol, 2.31 g/L $KH_2PO_4$, and 12.54 g/L $K_2HPO_4$) containing 50 µg/ml of kanamycin until a cell density of 0.4 to 0.6 $OD_{600}$ was reached. Expression of the RTA198 polynucleotide was induced by adding 1 mM isopropyl-β-D-thiogalactopyranoside (IPTG) at 25° C., for about 18 to about 20 hours. The cells were centrifuged in a Sorvall GS3 rotor at 6,000 rpm for 15 minutes at 4° C. The cell media was decanted and discarded. The pellet containing E. coli cells were bathed in TB medium with kanamycin and IPTG to create a cell paste that was frozen at −20° C. until further use. Generally, the frozen cell paste was stored for at least about 24 hours prior to protein purification.

As an "induction check" to ensure that RTA198 was being expressed, an aliquot of E. coli cells was analyzed using polyclonal antiserum specific for RTA and standard methods of sodium dodecyl sulfate polyacrylamide gel electrophoresis (SDS-PAGE) and Western blot analysis. The antiserum was affinity purified previously using dgRTA by conventional methods in the art. Briefly, wet E. coli cells were solubilized in 50 mM sodium phosphate buffer, pH 7.3, and centrifuged to give a soluble fraction (supernatant) and a pellet. The pellet was then solubilized by boiling in 6M urea, pH 7. RTA198 was detected by Western blot analysis in both the phosphate buffer soluble fraction, and in the phosphate buffer insoluble fraction.

C. Purification of RTA198

One (1) gram of cell paste was dissolved in 15 ml of an ice cold buffer solution comprising 50 mM sodium phosphate buffer and 2 mM ethylene diamine tetra-acetic acid (EDTA), pH 7.3. The cells were then sonicated and the homogenized cells were centrifuged using a Sorvall SS-34 rotor for 15,000 rpm for 15 minutes at 4° C. The supernatant was collected and syringe filtered (0.2 µm pore size).

A Pharmacia Mono-Q® 10/10 anion exchange column (Amersham-Pharmacia Biotech, Piscataway, N.J.) was pre-equilibrated with 50 mM sodium phosphate, pH 7.3, and 2 mM EDTA. The supernatant comprising RTA198 was applied and a step elution was run to 1M NaCl (0-1.0 min). RTA198 was found predominantly in the column flow-through.

The Mono-Q® 10/10 flow through was titrated to 0.6 ammonium sulfate (final concentration) using a stock solution of 3M ammonium sulfate, pH 7.0. This material was filtered (0.2 µm pore size), and subsequently applied to an equilibrated TosoHaas® phenyl hydrophobic interaction chromatography (HIC) column (Tosoh Biosep, Montgomeryville, Pa.) pre-equilibrated with 0.6 M ammonium sulfate, 50 mM sodium phosphate buffer, and 2 mM EDTA, pH 7. A gradient elution was run from 0.6 M to 0 M ammonium sulfate, 50 mM sodium phosphate buffer, 2 mM EDTA, pH 7 (0-30 min). All fractions showing protein by $OD_{280}$ absorbance were analyzed by reducing SDS-PAGE. Multiple fractions (4×4 ml) from the major HIC column peak comprised RTA198 which were then pooled and dialyzed against 50 mM Tris base/2 mM EDTA, pH 9.2.

The pooled HIC fractions were applied to a Pharmacia Mono-Q® 10/10 (Amersham-Pharmacia Biotech, Piscataway, N.J.) anion exchange column pre-equilibrated in 50 mM Tris base/2 mM EDTA, pH 9.2, and a step eluted to 0.4 M NaCl. The purified RTA198 was found almost exclusively in the flow-through fraction.

D. Characterization of Purified RTA198

Figure 2:
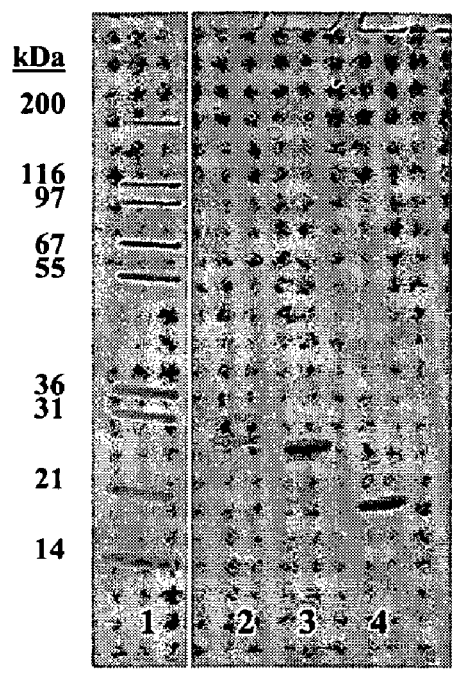
FIG. 2 is an SDS-PAGE that compares the heterogeneity of dgRTA, wt RTA, and RTA198 and RTA 1-33/44-198.

The flow-through fraction from the Mono-Q® 10/10 anion exchange column at pH 9.2 comprised greater than about 90% pure RTA198 as determined by SDS-PAGE stained with Coomassie blue and Western blots. The buffer was changed to 120 mM NaCl, 2.7 mM KCl, 10 mM $NaPO_4$, pH 7.4, by extensive dialysis (2L×3 changes of greater than about 3 hours at room temperature). Purified RTA198 was filtered (0.2 µm pore size) and stored sterile at 4° C. prior to animal studies. Total protein concentrations were determined using the Pierce micro-BCA assay (Pierce Chemical, Rockford, Ill.) (Smith, P. K., et al. (1985) Anal. Biochem. 150:76-85, which is herein incorporated by reference) relative to a bovine serum albumin standard curve. The purity of RTA198 obtained is shown in FIG. 2. Specifically, FIG. 2 is an SDS-PAGE result wherein lane 1 shows the molecular weight standards. To each lane, about 2 to about 4 μg of protein (200 kDa standard ladder, dgRTA, wt RTA, RTA198) as determined by a bicinchoninic acid assay (BCA) standard in the art. The gel is 10% (w/v) total acrylamide stained with Coomassie blue. Lane 2 is dgRTA, lane 3 is purified recombinant wt RTA, and lane 4 is RTA198. As shown, the RTA198 produced a clear dark band thereby indicating a high degree of homogeneity.

The purified RTA198 did not possess detectable levels of N-glycosidase activity as evidenced by the inability to disrupt protein synthesis in a cell-free, translation assay under conditions where either natural ricin (positive control) or isolated wt RTA (positive control) did show ribosome inactivation. See Langer, et al. (1996) Anal. Biochem. 243(1):150-153; and Hale (2001) Pharmacol. Toxicol. 88(5):255-260, which are herein incorporated by reference.

The RTA activity assay was conducted as described by Hale (2001) Pharmacol. Toxicol. 88(5):255-260. This assay takes advantage of the fact that the N-glycosidase activity of RTA can be monitored with an in vitro translation assay using the rabbit reticulocyte lysate system. See Barbieri et al. (1989) Biochem. J. 257:801-807, which is herein incorporated by reference. The assay measures the in vitro translation of the enzyme luciferase, as determined by the fluorescence produced when luciferase reacts with the substrate luciferin. Briefly, a translation lysate was prepared at 4° C. that contained nuclease-treated rabbit reticulocyte lysate, amino acid mixture, Rnasin ribonuclease inhibitor, nuclease-treated deionized water, and luciferase mRNA in a ratio of(v/v): 35:1:1:35:1, respectively (all available from Promega, Madison, Wis.).

Aliquots of RTA198 at several dilutions were added to the translation lysate in wells of a microtiter plate, and subsequently incubated at 30° C. in a moist chamber for 90 minutes. As negative controls to observe maximal fluorescence, some wells received phosphate buffered saline. As additional negative controls, some wells received several dilutions of RTB (ranging in final concentration from 0.06 to 17 nM RTB). As positive controls to observe decreased fluorescence, some wells contained the translation lysate as described without the luciferase mRNA. As additional positive controls to observe graded decrease in fluorescence, some wells received dilutions of RTA (ranging in final concentrations from 0.06 to 17 nM RTA). At the end of the incubation period, the luciferin substrate in commercial reaction buffer (Promega, Madison, Wis.) was added to all wells, and the relative fluorescence was recorded using a microtiter plate fluorimeter.

E. Vaccine Studies with RTA198

When RTA198 was administered to mice, purified RTA198 effectively protected animals from a challenge with about 5 to about 10 $LD_{50}$ of ricin by either intraperitoneal injection, or by whole-body aerosol delivery of ricin toxin.

Three groups of 20 female BALB/c mice were treated with i.m. injections of RTA198, dgRTA (positive control), or phosphate buffered saline (control vehicle). At 0, 4, and 8 weeks, the mice in each group were injected i.m. with 0.1-ml at the following concentration of test/control articles:

a. Group 1: 20 mice injected with 10 μg of RTA198 protein.
b. Group 2: 10 mice injected with 10 μg of RTA198 protein+0.2% alhydrogel.
c. Group 3: 20 mice injected with 10 μg of dgRTA protein.
d. Group 4: 20 mice injected with phosphate buffered saline.

At 2 weeks after the third dosing, 20 mice in treatment groups 1, 3, & 4 and 10 mice in treatment group 2 were anesthetized and 0.2 to about 0.3 ml of blood was collected by the periorbital sinus method and recorded. The blood was later used to measure the specific antibody concentrations and ricin neutralizing antibody titers.

One week after blood collection, the same mice were weighed and ten mice from treatment groups 1, 3, & 4 were injected intraperitoneally on body weight bases with 0.1 ml of a solution that contained 10 mouse $LD_{50}$ of ricin toxin D. The remaining 10 mice from each treatment group were exposed over ten minutes in a dynamic system to a liquid aerosol that supplied 5 to 10 mouse $LD_{50}$ of ricin toxin D. After exposure to ricin, daily cage side observations were made for survival rates.

The results are summarized in the following Table 1:

TABLE 1

RTA198 Protects Mice from Lethal Exposure to Ricin Toxin

| Antigen | Dose¶ | Survival (Alive/Total) | Mean Time to Death |
|---|---|---|---|
| Intraperitoneal Injection of 10 $LD_{50}$s of Ricin Toxin | | | |
| RTA198 | 10 μg | 9/10 §,⊥ | 1.67 Days |
| dgRTA | 10 μg | 10/10 | >14 Days |
| phosphate buffered saline | 0.1 ml | 0/10 | 0.83 ± 0.02‡ Days |
| Aerosol Whole Body Exposure to Between 5 and 10 $LD_{50}$s of Ricin Toxin | | | |
| RTA198 | 10 μg | 10/10 §,⊥ | >14 Days |
| RTA198 + 0.2% Alhydrogel | 10 μg | 10/10 §,⊥ | >14 Days |
| dgRTA | 10 μg | 10/10 | >14 Days |
| phosphate buffered saline | 0.1 ml | 0/10 | 3.77 Days |

¶Three intramusclar injection at 0, 4, & 8 weeks
‡Average ± standard error
§ Significantly different (p < 0.01) from phosphate buffered saline controls by Fisher's Exact Test
⊥Not significantly different (p > 0.05) from dqRTA by Fisher's Exact Test Administration of the purified RTA198 without an adjuvant had no obvious, untoward effects on the mice as noted by survival from three immunizations, weight gain, physical appearance, food consumption, and normal activity in comparison to phosphate buffered saline controls. Vaccinated animals survived without co-administration of an adjuvant (in these experiments, the adjuvant was Alhydrogel® 2% $Al_2O_2$ available from Siperfos Biosector). Thus, RTA198 may be used to elicit an immune response in a subject and may be used as a safe and effective ricin vaccine.

Serum anti-ricin IgG antibody concentrations were measured by a direct method ELISA for the detection of ricin-specific IgG immunoglobulin in mouse sera. Specifically, ricin stock solution (5 mg/ml) (Vector Laboratories, Inc., Burlington, Calif.) was diluted 1:1000 in ELISA coating buffer and 100 μl was added to each well of a plate. The plate was stored at about 12 to about 48 hours at about 4° C. Seven concentrations of mouse anti-ricin serum (Perimmune Inc., Rockville, Md.) were prepared and standardized to provide a suitable standard curve for the ELISA. Positive and negative mouse anti-ricin serum controls were prepared and used.

Fresh dilutions of unknown sera were prepared by adding 12.5 μl of serum to 987.5 μl of MASP buffer. Optimal sera dilutions may be determined by conventional methods in the art. The plate was washed 3 times with 0.2 ml/well of ELISA wash buffer. To each well, 200 μl of 5% skim milk buffer was added. The plate was covered and incubated in a moist chamber at about 37° C. for 1 hour. The plate was then washed 3 times with 0.2 ml/well ELISA wash buffer. Then serial dilutions of the unknowns and controls and standards were added to the wells. The plate was incubated at about 37° C. for about 1 hour. The plate was then washed 3 times with 0.2 ml/well ELISA wash buffer. To each well, 100 μl of goat anti-mouse IgG (H+L) conjugate (Kirkegaard & Perry Laboratories, Gaithersburg, Md.) was added and then incubated at room temperature for about 1 hour. The plate was then washed 3 times with 0.2 ml/well ELISA wash buffer. To each well, 100 μl of ABTS peroxidase substrate (Kirkegaard & Perry Laboratories, Gaithersburg, Md.) was added and then allowed to stand at room temperature for about 40 minutes. Then 100 μl of ABTS peroxidase stop solution was added to each well. The plate was read using a microplate reader at 405 nm.

The results are summarized in the following Table 2:

TABLE 2

RTA198 Protects Mice from Lethal Exposure to Ricin Toxin

| Antigen | Dose¶ | Survival (Alive/Total) | Anti-Ricin IgG (mg/ml) |
|---|---|---|---|
| Intraperitoneal Injection of 10 $LD_{50}$s of Ricin Toxin | | | |
| RTA198 | 10 μg | 9/10 §,⊥ | 0.32 ± 0.06‡* |
| dgRTA | 10 μg | 10/10 | 3.04 ± 0.36 |
| phosphate buffered saline | 0.1 ml | 0/10 | <0.001 |
| Aerosol Whole Body Exposure to Between 5 and 10 $LD_{50}$s of Ricin Toxin | | | |
| RTA198 | 10 μg | 10/10 §,⊥ | 0.18 ± 0.04* |
| RTA198 + 0.2% Alhydrogel | 10 μg | 10/10 §,⊥ | 0.51 ± 0.14*v |
| dgRTA | 10 μg | 10/10 | 4.64 ± 0.50 |
| phosphate buffered saline | 0.1 ml | 0/10 | <0.01 |

¶Three intramusclar injection at 0, 4, & 8 weeks
‡Average ± standard error
§ Significantly different ($p < 0.01$) from phosphate buffered saline controls by Fisher's Exact Test
⊥Not significantly different ($p > 0.05$) from dgRTA by Fisher's Exact Test
*Significantly different ($p < 0.01$) from chemically dgRTA controls by Unpaired t Test
vSignificantly different ($p < 0.01$) from non-adjuvant 1-198 & 33-44 deletion wild-type rRTA by Unpaired t Test

EXAMPLE 2

Construction and Analysis of RTA1-33/44-198

Calculations of solvation free energies indicated that the protein RTA198 is likely to be more stable in solvent water than the native RTA fold. It was noticed, however, that water was likely to fill several protein cavities not initially exposed to solvent in the native fold. Thus, a structural element of concern was the loop region comprising the amino acid residues from about position 33 to about 44. The loop region comprises a β-hairpin and several charged residues and the overall structure has a hydrophobic character. Thus, it was hypothesized that this loop region may be deleted to give a RTA comprising amino acid residues 1-33 and 44-198 (RTA1-33/44-198) that will retain the compactness and activity of RTA198.

A. DNA Cloning, Sequencing, and Expression of RTA1-33/44-198

DNA cloning, sequencing, and expression similar to that disclosed in Example 1 were used. Briefly, mutagenesis was done using the QuickChange kit commercially available from Stratagene (La Jolla, Calif.) based upon the polymerase chain reaction (PCR) method. Starting with the RTA198 construct described in Example 1, a pair of PCR oligonucleotide primers selected to delete 10 amino acids at position 34-43 were used. The sense PCR oligonucleotide used was: 5' CTG TCA GAG GTA GAT TGA CTG TCT TGC CTA ACA GAG TTG G 3' (SEQ ID NO:14). The antisense PCR oligonucleotide used was: 5' CCA ACT CTG TTA GGC AAG ACA GTC AAT CTA CCT CTG ACA G 3' (SEQ ID NO:15). Mutagenesis was conducted under contract by Clinical Research Management (Frederick, Md.).

After eliminating template DNA, 1 μl sample of the PCR mixture containing the mutated polynucleotide is used to transform *E. coli* XL1-Blue competent *E. coli* cells (Stratagene). The resultant mutated polynucleotide was purified using a commercial Miniprep kit (Qiagen, Valencia, Calif.) and sequenced using conventional methods to confirm that only the desired changes were made. The polynucleotide products were purified, ligated to a commercial expression vector based upon the T7 promoter system (Studier, et al. (1990) supra), and then used to transform competent *E. coli* BL21 DE3 strain (Invitrogen, Calif.).

B. Expression of RTA1-33/44-198

The transformed *E. coli* BL 21 cells were cultured in TB media comprising 50 μg/ml of kanamycin until a cell density of 0.4 to 0.6 $OD_{600}$ was reached. Expression of the RTA1-33/44-198 polynucleotide was induced using 1 mM IPTG at 25° C., for about 18 to about 20 hours. The cells were centrifuged in a Sorvall GS3 rotor at 6,000 rpm for 15 minutes at 4° C. The cell media was decanted and discarded. The pellet containing *E. coli* cells were bathed in TB medium with kanamycin and IPTG to create a cell paste that was frozen at −20° C. until further use. Generally, the frozen cell paste was stored for at least about 24 hours prior to protein purification.

As an "induction check" to ensure that RTA1-33/44-198 was being expressed was performed according to Example 1B above. Immunoreactive protein corresponding to RTA1-33/44-198 was found in both the phosphate buffer soluble and the insoluble fractions.

C. Purification of RTA1-33/44-198

One (1) gram (wet weight) of cell paste was dissolved in 15 ml of an ice cold buffer solution comprising 50 mM sodium phosphate buffer and 2 mM EDTA, pH 7.3. The cells were then sonicated and the homogenized cells were centrifuged using a Sorvall SS-34 rotor for 15,000 rpm for 15 minutes at 4° C. The supernatant was collected and syringe filtered (0.2 μm pore size).

A Pharmacia Mono-Q® 10/10 anion exchange column (Amersham-Pharmacia Biotech, Piscataway, N.J.) was pre-equilibrated with 50 mM sodium phosphate, pH 7.3, and 2 mM EDTA. The supernatant comprising RTA1-33/44-198 was applied and a step elution was run to 1M NaCl (0-1.0 min). RTA1-33/44-198 was found predominantly in the column flow-through as determined by SDS-PAGE and Western blots.

The Mono-Q® 10/10 flow-through was pooled and the buffer was changed by dialysis to 50 mM MES, 2 mM EDTA, pH 6.4. The material was syringe filtered (0.2 μm pore size), and loaded onto an equilibrated Pharmacia Mono-S® 5/5 cation exchange column (50 mM MES, 2 mM EDTA, pH 6.4). Protein was eluted from the column using a NaCl gradient (0-500 mM NaCl in 30 minutes). Purified RTA1-33/44-198 began to elute by 20 mM and was completely eluted by about 150 mM NaCl. All fractions showing protein by $OD_{280}$ absorbance were analyzed by reducing SDS-PAGE.

D. Characterization of Purified RTA1-33/44-198

Figure 3:
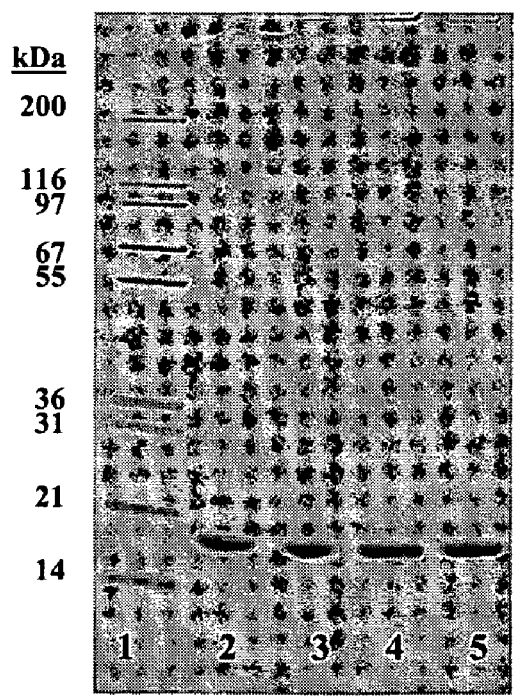
FIG. 3 is an SDS-PAGE that exhibits the consistency and reproducibility of making the polypeptides of the present invention as exemplified with RTA1-33/44-198.

Fractions from the Mono-S® column that comprised greater than about 90% pure RTA1-33/44-198, as judged by Coomassie blue stained gels, were pooled. The buffer was changed to a buffer solution comprising 120 mM NaCl, 2.7 mM KCl, 10 mM $NaPO_4$, pH 7.4, by extensive dialysis (2L×3 changes of greater than about 3 hours at room temperature). Purified RTA1-33/44-198 was filtered (0.2 μm pore size) and stored sterile at 4° C. prior to animal studies. Total protein concentrations were determined using the Pierce micro-BCA assay, relative to a bovine serum albumin standard curve. Purity and consistency of lots of RTA1-33/44-198 obtained by this method is demonstrated in FIG. 3. Specifically, FIG. 3 is an SDS-PAGE result wherein lane 1 shows the molecular weight standards. Lanes 2-5 show about 2 μg of RTA1-33/44-198 from four different lots that were expressed and purified independent of each other. The gel is 10% (w/v) total acrylamide stained with Coomassie blue. As shown, the each lane produced a clear dark band, which bands were consistently similar to each other. Therefore, the production and purification of the polypeptides of the present invention are reproducible and suitable for vaccine production.

To determine whether RTA1-33/44-198 exhibited N-glycosidase activity, the assay according to Example 1D above was conducted. Purified RTA1-33/44-198 did not exhibit any detectable N-glycosidase activity as evidenced by inability to disrupt protein synthesis in a cell-free, translation assay under conditions where either natural ricin (positive control) or isolated RTA (positive control) did show ribosome inactivation. See Langer, et al. (1996) supra; and Hale (2001) supra.

E. Vaccine Studies with RTA1-33/44-198

When RTA1-33/44-198 was administered, purified RTA1-33/44-198 effectively protected animals from a challenge with about 5 to about 10 $LD_{50}$ of ricin by either intraperitoneal injection, or by whole-body aerosol delivery of ricin toxin.

Three groups of 20 female BALB/c mice were treated with i.m. injections of RTA1-33/44-198, dgRTA (positive control), or phosphate buffered saline (control vehicle). At 0, 4, and 8 weeks, the mice in each group were injected i.m. with 0.1-ml at the following concentration of test/control articles:

a. Group 1: 20 mice injected with 10 μg of RTA1-33/44-198 protein.
b. Group 2: 20 mice injected with 10 μg of RTA1-33/44-198 protein+0.2% alhydrogel.
c. Group 3: 20 mice injected with 10 μg of dgRTA protein.
d. Group 4: 20 mice injected with phosphate buffered saline.

At 2 weeks after the third dosing, 20 mice were anesthetized and 0.2 to about 0.3 ml of blood was collected by the periorbital sinus method and recorded. The blood was later used to measure the specific antibody concentrations and ricin neutralizing antibody titers.

One week after blood collection, same mice were weighed and ten mice from each treatment group were injected intraperitoneally on body weight bases with 0.1 ml of a solution that contained 10 mouse $LD_{50}$ of ricin toxin D. The remaining 10 mice from each treatment group were exposed over ten minutes in a dynamic system to a liquid aerosol that supplied 5 to 10 mouse $LD_{50}$ of ricin toxin D. After exposure to ricin, daily cage side observations were made for survival rates.

The results are provided in the following Table 3:

TABLE 3

RTA1-33/44-198 Protects Mice from Lethal Exposure to Ricin Toxin

| Antigen | Dose[¶] | Survival (Alive/Total) | Mean Time to Death |
|---|---|---|---|
| Intraperitoneal Injection of 10 $LD_{50}$s of Ricin Toxin | | | |
| RTA1-33/44-198 | 10 μg | 10/10 §,⊥ | >14 Days |
| RTA1-33/44-198 + 0.2% Alhydrogel | 10 μg | 10/10 §,⊥ | >14 Days |
| dgRTA | 10 μg | 10/10 | >14 Days |
| phosphate buffered saline | 0.1 ml | 0/10 | 0.74 ± 0.01‡ Days |
| Aerosol Whole Body Exposure to Between 5 and 10 $LD_{50}$s of Ricin Toxin | | | |
| RTA1-33/44-198 | 10 μg | 10/10 §,⊥ | >14 Days |
| RTA1-33/44-198 + 0.2% Alhydrogel | 10 μg | 10/10 §,⊥ | >14 Days |
| dgRTA | 10 μg | 10/10 | >14 Days |
| phosphate buffered saline | 0.1 ml | 0/10 | 3.84 ± 0.07 Days |

[¶]Three intramusclar injection at 0, 4, & 8 weeks
‡Average ± standard error
§ Significantly different (p < 0.01) from phosphate buffered saline controls by Fisher's Exact Test
⊥Not significantly different (p > 0.05) from dgRTA by Fisher's Exact Test Administration of the purified RTA1-33/44-198 without an adjuvant had no obvious, untoward effects on the mice as noted by survival from three immunizations, weight gain, physical appearance, food consumption, and normal activity in comparison to phosphate buffered saline controls. Vaccinated animals survived without co-administration of an adjuvant (in these experiments, the adjuvant was Alhydrogel® 2% ($Al_2O_3$) available from Siperfos Biosector). Thus, RTA1-33/44-198 may be used to elicit an immune response in a subject and may be used as a safe and effective ricin vaccine.

Serum anti-ricin IgG antibody concentrations were measured by the direct method ELISA for the detection of ricin-specific IgG immunoglobulin in mouse sera described above. The results are provided in the following Table 4:

TABLE 4

RTA1-33/44-198 Protects Mice from Lethal Exposure to Ricin Toxin

| Antigen | Dose[¶] | Survival (Alive/Total) | Anti-Ricin IgG (mg/ml) |
|---|---|---|---|
| Intraperitoneal Injection of 10 $LD_{50}$s of Ricin Toxin | | | |
| RTA1-33/44-198 | 10 μg | 10/10 §,⊥ | 0.28 ± 0.08[⊕] |
| RTA1-33/44-198 + 0.2% Alhydrogel | 10 μg | 10/10 §,⊥ | 0.56 ± 0.10[⊕,ν] |
| dgRTA | 10 μg | 10/10 | 1.12 ± 0.11 |
| phosphate buffered saline | 0.1 ml | 0/10 | <0.01 |
| Aerosol Whole Body Exposure to Between 5 and 10 $LD_{50}$s of Ricin Toxin | | | |
| RTA1-33/44-198 | 10 μg | 10/10 §,⊥ | 0.15 ± 0.04[⊕] |
| RTA1-33/44-198 + 0.2% Alhydrogel | 10 μg | 10/10 §,⊥ | 0.81 ± 0.12[⊕,ν,•] |
| dgRTA | 10 μg | 10/10 | 0.95 ± 0.15 |
| phosphate buffered saline | 0.1 ml | 0/10 | <0.01 |

[¶]Three intramusclar injection at 0, 4, & 8 weeks
‡Average ± standard error
§ Significantly different (p < 0.01) from phosphate buffered saline controls by Fisher's Exact Test
⊥Not significantly different (p > 0.05) from dgRTA by Fisher's Exact Test
⊕Significantly different (p < 0.01) from chemically dgRTA controls by Unpaired t Test
νSignificantly different (p < 0.01) from non-adjuvant 1-198 & 33-44 deletion wild-type rRTA by Unpaired t Test
•Not significantly different (p > 0.05) from chemically dgRTA by Unpaired t Test Additionally, since RTA1-33/44-98 maintains a similar conformation and immunogenic activity as RTA198, polypeptides of the present invention such as RTA1-33/44-98 may be used as stable structural scaffolds to present antigenic determinants of ricin for use in immunogenic compositions such as ricin vaccines.

EXAMPLE 3

Protein Aggregation

To compare the relative amounts of protein aggregation in solutions of the novel RTA polypeptides versus dgRTA or recombinant RTA the following experiment may be conducted. The amounts and types of aggregates formed by the vaccine candidates may be quantified as a function of protein concentration and time under various conditions of fixed buffer composition, ionic strength, and pH. A combination of analytical size-exclusion chromatography (SEC) may be used with on-line multi-angle light scattering (MALS) detection. The SEC-MALS provides a measure of the molar mass of proteins in solution because the light scattering response is directly proportional to the weight-averaged molar mass (Mw) of the protein sample multiplied by the sample concentration.

Briefly, solutions of protein samples at a concentration of about 0.4 to about 1.5 mg/ml in 0.067 M Na/K phosphate, pH 7.5 are separated using standard high performance liquid chromatographic methodology with a flow rate of about 0.5 to about 1.0 ml/min. Protein species are detected with an in-line standard UV/VIS HPLC detector, and the relative refractive indices of the sample components are determined from an in-line interferometric refractometer. Light scattering data are collected at many wavelengths, averaged, and evaluated using an in-line MALS instrument. Aggregates are quantified by molar mass for each protein sample.

EXAMPLE 4

Protein Folding Stability

To compare the relative protein folding stability of the novel RTA polypeptides versus dgRTA or recombinant RTA the following may be conducted. Relative protein folding stability is measured indirectly by comparing the amount of energy (proportional to temperature) required to unfold each polypeptide under various conditions of ionic strength or pH. The extent of protein unfolding is assessed indirectly by circular dichroism (CD) spectroscopy. Briefly, CD scans of protein samples are performed in a spectropolarimeter, fitted with peltier thermal control unit, using 0.2 mm and 1 cm path length quartz cuvettes, respectively, for near and far UV measurements. Solutions of purified polypeptide are used at a concentration of about 0.5 mg/ml in 0.067 M Na/K phosphate, pH 7.5. The initial scans provide baseline spectra and corroborate that the protein samples are folded. Subsequently, protein samples are intentionally and slowly unfolded by increasing the cuvet temperature by means of the thermal control unit. Temperature-induced changes in protein secondary structure are assessed indirectly by monitoring the change in mean residue ellipticity at 222 nm. From these data, one may calculate and compare the temperature (Tm) at which 50% of the protein is unfolded. If the novel RTA polypeptides are found to fold and unfold reversibly, then one may also calculate and compare the thermodynamic and enthalpic constants for protein folding.

EXAMPLE 5

Hydrophobic Surface Exposure

To compare the relative exposure of hydrophobic surfaces among the novel RTA polypeptides of the present invention versus dgRTA, or recombinant RTA the following (indirect) assay may be conducted by measuring the amount of 1-anilino-8-naphthalenesulfonic acid (ANS) bound to each polypeptide under defined conditions of buffer composition, pH, ionic strength and temperature. Increased binding of ANS, is indicative of increased availability of hydrophobic surfaces, and bound dye can be differentiated from unbound dye on the basis of fluorescence. Briefly, 2 µl of 0.1 mM ANS in acetonitrile is added to 200 µl of 0.5 µM RTA polypeptide in 0.067 M Na/K phosphate, pH 7.5. Fluorescence is measured using a spectrofluorimeter at room temperature; the excitation wavelength is 390 nm, and the emission spectrum is evaluated between 400 and 600 nm.

EXAMPLE 6

Effects of Storage Time on Biophysical Properties

To evaluate how the biophysical properties of the novel RTA polypeptides of the present invention may vary as a function of storage time (such as over the course of 24 months) and storage temperature (such as at about 2 to about 8, 25 and 40° C.) in different storage formulations the following assay may be conducted. The number of possible storage formulations is very large; therefore, only a subset of formulations using a sparse matrix that isolates selected variables are tested. These variables might include the buffer composition, the ionic strength, the pH, or the presence or absence of preferred adjuvants. Biophysical properties of the novel RTA polypeptides to be observed under different storage conditions may include, relative molecular mass of polypeptides, apparent isoelectric point of polypeptides (net charge), extent of self-aggregation, protein folding stability, and exposure of hydrophobic surfaces. These can be evaluated as described using SDS-PAGE, native PAGE, isoelectric focusing, light scattering, ANS dye binding, and circular dichroism spectroscopy.

EXAMPLE 7

Elucidation of Three-Dimensional Structure

To determine the precise three-dimensional structures of the novel RTA polypeptides of the present invention near atomic resolution single crystal, macromolecular X-ray crystallographic methods may be used. Protein crystals of novel RTA polypeptides are obtained using the hanging-drop vapour-diffusion method, and a sparse matrix of crystallization conditions. Protein crystals are flash-frozen in liquid nitrogen prior to data collection at 100° K. Data may be collected at the National Synchrotron Light Source at Brookhaven National Laboratory. Structure solution will be attempted using molecular replacement and the coordinates of RTA (Protein Databank, PDB) s a starting model. The structures may be refined by a combination of simulated annealing and molecular dynamics with a maximum likelihood target function, using the CNS program suite. See Adams, P. D., et al. (1997) PNAS USA 94:5018-23; and Brunger, A. T., et al. (1998) Acta Cryst. D54, 905-921.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. An isolated polypeptide consisting of SEQ ID NO:10, SEQ ID NO:10 wherein the first amino acid residue and the last amino acid residue are deleted, or SEQ ID NO:10 wherein the last amino acid residue is deleted.

2. The polypeptide of claim 1, made by recombinant DNA techniques.

3. A pharmaceutical composition comprising at least one polypeptide of claim 1 and a pharmaceutically acceptable vehicle.

4. The pharmaceutical composition of claim 3, further comprising an adjuvant.

5. A kit comprising at least one of the following:
   a) the polypeptide of claim 1; or
   b) the polypeptide of claim 1 and a pharmaceutically acceptable vehicle; packaged together with instructions for use.

* * * * *